(12) United States Patent
Uramatsu et al.

(10) Patent No.: US 10,632,074 B2
(45) Date of Patent: Apr. 28, 2020

(54) COMPOSITE GRANULATED PRODUCT INCLUDING SUGAR OR SUGAR ALCOHOL, SWELLING BINDER, DISINTEGRATING AGENT AND HIGHLY ABSORBENT EXCIPIENT, AND METHOD FOR MANUFACTURING COMPOSITE GRANULATED PRODUCT

(71) Applicant: DAIDO CHEMICAL CORPORATION, Osaka-shi, Osaka (JP)

(72) Inventors: Shunji Uramatsu, Osaka (JP); Toshinobu Uemura, Osaka (JP); Masakazu Morizane, Osaka (JP); Toshio Shimamoto, Osaka (JP)

(73) Assignee: DAIDO CHEMICAL CORPORATION, Osaka (JP)

( * ) Notice: Subject to any disclaimer, the term of this patent is extended or adjusted under 35 U.S.C. 154(b) by 0 days.

(21) Appl. No.: 15/765,808

(22) PCT Filed: Oct. 4, 2016

(86) PCT No.: PCT/JP2016/079490
§ 371 (c)(1),
(2) Date: Apr. 4, 2018

(87) PCT Pub. No.: WO2017/061426
PCT Pub. Date: Apr. 13, 2017

(65) Prior Publication Data
US 2018/0280304 A1 Oct. 4, 2018

(30) Foreign Application Priority Data
Oct. 5, 2015 (JP) .................. 2015-197770

(51) Int. Cl.
| A61K 9/20 | (2006.01) |
| A61K 9/16 | (2006.01) |
| A61K 47/02 | (2006.01) |
| A61K 45/00 | (2006.01) |
| A61K 9/00 | (2006.01) |

(52) U.S. Cl.
CPC .......... *A61K 9/1652* (2013.01); *A61K 9/0056* (2013.01); *A61K 9/1611* (2013.01); *A61K 9/1623* (2013.01); *A61K 9/1635* (2013.01); *A61K 9/2018* (2013.01); *A61K 9/2027* (2013.01); *A61K 9/2054* (2013.01); *A61K 9/2095* (2013.01); *A61K 45/00* (2013.01); *A61K 47/02* (2013.01)

(58) Field of Classification Search
CPC ...... A61K 9/20; A61K 9/2004; A61K 9/2018; A61K 9/205; A61K 9/2054; A61K 9/2059; A61K 9/2077; A61K 9/2086; A61K 9/209; A61K 9/2095

See application file for complete search history.

(56) References Cited

U.S. PATENT DOCUMENTS

| 8,337,892 B1* | 12/2012 | Couaraze | A61K 9/5078 424/464 |
| 2005/0090473 A1* | 4/2005 | Devane | A61K 9/2054 514/150 |
| 2007/0275058 A1 | 11/2007 | Tanaka et al. | |
| 2010/0189787 A1 | 7/2010 | Safadi et al. | |
| 2012/0003309 A1 | 1/2012 | Colledge et al. | |

FOREIGN PATENT DOCUMENTS

| JP | 06-030975 A | 2/1994 |
| JP | 2011-026311 A | 2/2011 |
| JP | 2012-510483 A | 5/2012 |
| JP | 2012-515775 A | 7/2012 |
| JP | 2015-078182 A | 4/2015 |
| JP | 2015-098467 A | 5/2015 |
| JP | 2006-282551 A | 10/2016 |
| WO | 2005/037254 A1 | 4/2005 |
| WO | 2007/029376 A1 | 3/2007 |
| WO | 2008/078726 A1 | 7/2008 |
| WO | 2014/058046 A1 | 4/2014 |

OTHER PUBLICATIONS

Extended European Search Report dated Apr. 3, 2019 for European Patent Application No. 16853580.5, 11 pages.
Badgujar et al., "The technologies used for developing orally disintegrating tablets: A review", ACTA Pharmaceutica, 2011, vol. 61, No. 2, pp. 117-139.
International Search Report dated Dec. 27, 2016 from International Application No. PCT/JP2016/079490 (including English translation), 4 pages.
Noriyuki Namiki "Pharmaceutical Technology Required from Clinical Side—Development of the Orally Disintegrating Tablets to be Easily Taken—", Journal of Pharmaceutical Machinery and Engineering, 2012, vol. 21, No. 4, 10 pages with English translation of Abstract.
Office Action dated Nov. 24, 2015 from Japanese Application No. 2015-197770, 13 pages with English translation.

* cited by examiner

*Primary Examiner* — Micah Paul Young
(74) *Attorney, Agent, or Firm* — MH2 Technology Law Group, LLP

(57) ABSTRACT

The present invention provides a composite granulated product that is optimal for allowing a tablet, preferably an orally disintegrating tablet (OD tablet) to be excellent in disintegrability and have proper hardness. The composite granulated product includes a sugar or a sugar alcohol, a swelling binder, a disintegrating agent, and a highly absorbent excipient.

15 Claims, 2 Drawing Sheets

COMPOSITE GRANULATED PRODUCT INCLUDING SUGAR OR SUGAR ALCOHOL, SWELLING BINDER, DISINTEGRATING AGENT AND HIGHLY ABSORBENT EXCIPIENT, AND METHOD FOR MANUFACTURING COMPOSITE GRANULATED PRODUCT

CROSS-REFERENCE TO RELATED APPLICATIONS

This application is a U.S. National Stage application of PCT/JP2016/079490 filed 4 Oct. 2016, which claims priority to Japanese Application No. 2015-197770 filed 5 Oct. 2015, the entire disclosures of which are hereby incorporated by reference in their entireties.

TECHNICAL FIELD

The present invention relates to a composite granulated product including a sugar or a sugar alcohol, a swelling binder, a disintegrating agent, and a highly absorbent excipient, and to a manufacturing method therefor.

BACKGROUND ART

As a final form of a solid pharmaceutical, there is known a tablet.

Among tablets, an orally disintegrating tablet (OD tablet) is a dosage form that easily disintegrates and is easy to take. The OD tablet generally has low tablet hardness, and hence there is a demand for prevention of cracking of the OD tablet in handling of the tablet at a production site and later in a medical setting (Non Patent Literature 1).

CITATION LIST

Non-Patent Literature

NPL 1: Journal of Pharmaceutical Machinery and Engineering, 2012, Vol. 21, No. 4, Special issue on orally disintegrating formulations

SUMMARY OF INVENTION

Technical Problem

A primary object of the present invention is to provide a composite granulated product that is optimal for allowing a tablet, preferably an orally disintegrating tablet (OD tablet) to be excellent in disintegrability and show proper hardness.

Solution to Problem

The inventors of the present invention have made extensive investigations in view of the problem of the related art described above.

Then, the inventors of the present invention have found that, when an OD tablet is produced using a composite granulated product including a sugar or a sugar alcohol, a swelling binder, a disintegrating agent, and a highly absorbent excipient, the OD tablet has high hardness and is also excellent in disintegrability.

The inventors of the present invention have also found that, particularly when an OD tablet is produced using a composite granulated product obtained by performing wet granulation in a binding solution using a sugar or a sugar alcohol, a swelling binder, a disintegrating agent, and an excipient, then adding layering granulation with a highly absorbent excipient, and further performing layering granulation (surface-modifying granulation) with a disintegrating agent, the OD tablet has high hardness and is also excellent in disintegrability.

The present invention is directed to the following composite granulated product and manufacturing method therefor.

First Group of Inventions

Item 1.

A manufacturing method for a composite granulated product including a sugar or a sugar alcohol, a swelling binder, a disintegrating agent, and a highly absorbent excipient, the manufacturing method including the steps of:

(1) performing wet granulation by mixing a sugar or a sugar alcohol, a swelling binder, and a first disintegrating agent using a binding solution;

(2) performing granulation with addition of a highly absorbent excipient to a granulated product obtained in the step (1); and (3) performing granulation with addition of a second disintegrating agent to a granulated product obtained in the step (2), the first disintegrating agent and the second disintegrating agent each being at least one kind of component selected from the group consisting of hydroxypropyl cellulose, crospovidone, starch, croscarmellose sodium, carmellose calcium, carmellose, partially pregelatinized starch, carboxymethyl starch sodium, and sodium starch glycolate.

Item 2.

The manufacturing method for a composite granulated product according to the item 1, in which the sugar or the sugar alcohol is at least one kind of component selected from the group consisting of D-mannitol, trehalose, xylitol, erythritol, lactose, and sucrose.

Item 3.

The manufacturing method for a composite granulated product according to the item 1 or 2, in which the swelling binder is at least one kind of component selected from the group consisting of a polyvinyl alcohol-based polymer, partially pregelatinized starch, hydroxypropyl cellulose, and crystalline cellulose.

Item 4.

The manufacturing method for a composite granulated product according to any one of the items 1 to 3, in which the swelling binder has an average particle diameter of from 10 μm to 200 μm.

Item 5.

The manufacturing method for a composite granulated product according to any one of the items 1 to 4, in which the highly absorbent excipient is at least one kind of component selected from the group consisting of light anhydrous silicic acid, hydrated silicon dioxide, calcium silicate, magnesium aluminometasilicate, starch, calcium carbonate, kaolin, silicic acid, potassium hydrogen phosphate, calcium hydrogen phosphate, sodium hydrogen phosphate, dipotassium phosphate, disodium phosphate, potassium dihydrogen phosphate, calcium dihydrogen phosphate, sodium dihydrogen phosphate, calcium lactate, magnesium aluminosilicate, calcium silicate, and magnesium silicate.

Item 6.

The manufacturing method for a composite granulated product according to any one of the items 1 to 5, in which the first disintegrating agent is hydroxypropyl cellulose, and the second disintegrating agent is at least one kind of component selected from the group consisting of starch, crospovidone, and croscarmellose sodium.

Item 7.

The manufacturing method for a composite granulated product according to any one of the items 1 to 6, in which the composite granulated product is a composite granulated product for an orally disintegrating tablet.

Item 8.

A manufacturing method for a granule for tableting, including (4) a step of adding and mixing at least one kind of hardness modifier selected from the group consisting of crystalline cellulose, a D-mannitol granulated product, and isomalt into a composite granulated product obtained by the manufacturing method for a composite granulated product of any one of the items 1 to 7.

Item 9.

The manufacturing method for a granule for tableting according to the item 8, in which the granule for tableting is a granule for tableting for an orally disintegrating tablet.

Item 10.

A manufacturing method for a tablet, including mixing:
a medicinal component and functional particles; and
a composite granulated product obtained by the manufacturing method for a composite granulated product of any one of the items 1 to 6, or
a described granule for tableting obtained by the manufacturing method for a granule for tableting of the item 8.

Item 11.

The manufacturing method for a tablet according to the item 10, in which the functional particles are at least one kind of component selected from the group consisting of bitterness-masking particles and sustained-release particles.

Item 12.

The manufacturing method for a tablet according to the item 10 or 11, further including adding and mixing a lubricant.

Item 13.

The manufacturing method for a tablet according to any one of the items 10 to 12, in which the tablet is an orally disintegrating tablet.

Item 14.

A composite granulated product, which is manufactured by the manufacturing method for a composite granulated product of any one of the items 1 to 7.

Item 15.

A granule for tableting, which is manufactured by the manufacturing method for a granule for tableting of the item 8 or 9.

Second Group of Inventions

Item 1.

A composite granulated product, including a sugar or a sugar alcohol, a swelling binder, a disintegrating agent, and a highly absorbent excipient.

Item 2.

The composite granulated product according to the item 1, in which the compositing is treatment involving the following steps:
(1) performing wet granulation by mixing a sugar or a sugar alcohol, a swelling binder, and a first disintegrating agent using a binding solution;
(2) performing granulation with addition of a highly absorbent excipient to a granulated product obtained in the step (1); and
(3) performing granulation with addition of a second disintegrating agent to a granulated product obtained in the step (2).

Item 3.

The composite granulated product according to the item 1 or 2, in which the sugar or the sugar alcohol is at least one kind of component selected from the group consisting of D-mannitol, trehalose, xylitol, erythritol, lactose, and sucrose.

Item 4.

The composite granulated product according to any one of the items 1 to 3, in which the swelling binder is at least one kind of component selected from the group consisting of a polyvinyl alcohol-based polymer, partially pregelatinized starch, hydroxypropyl cellulose, and crystalline cellulose.

Item 5.

The composite granulated product according to any one of the items 1 to 4, in which the disintegrating agent is at least one kind of component selected from the group consisting of hydroxypropyl cellulose, crospovidone, starch, croscarmellose sodium, carmellose calcium, carmellose, and partially pregelatinized starch.

Item 6.

The composite granulated product according to any one of the items 1 to 5, in which the highly absorbent excipient is at least one kind of component selected from the group consisting of light anhydrous silicic acid, hydrated silicon dioxide, calcium silicate, and magnesium aluminometasilicate.

Item 7.

The composite granulated product according to any one of the items 1 to 6, in which the swelling binder has an average particle diameter of from 10 μm to 200 μm.

Item 8.

A granule for tableting, including the composite granulated product of any one of the items 1 to 7, and at least one kind of hardness modifier selected from the group consisting of crystalline cellulose, a D-mannitol granulated product, and isomalt.

Item 9.

The composite granulated product according to any one of the items 1 to 7, in which the composite granulated product is a composite granulated product for an orally disintegrating tablet.

Item 10.

The granule for tableting according to the item 8, in which the granule for tableting is a granule for tableting for an orally disintegrating tablet.

Item 11.

A tablet, including:
a medicinal component and functional particles; and
the composite granulated product of any one of the items 1 to 7, or the granule for tableting of the item 8.

Item 12.

The tablet according to the item 11, in which the functional particles are at least one kind of component selected from the group consisting of bitterness-masking particles and sustained-release particles.

Item 13.

The tablet according to the item 11 or 12, in which the tablet is an orally disintegrating tablet.

Item 14.

A manufacturing method for a composite granulated product including a sugar or a sugar alcohol, a swelling binder, a disintegrating agent, and a highly absorbent excipient,
the manufacturing method including the steps of:
(1) performing wet granulation by mixing a sugar or a sugar alcohol, a swelling binder, and a first disintegrating agent using a binding solution;

(2) performing granulation with addition of a highly absorbent excipient to a granulated product obtained in the step (1); and (3) performing granulation with addition of a second disintegrating agent to a granulated product obtained in the step (2).

Item 15.

A manufacturing method for a granule for tableting, further including (4) a step of adding and mixing at least one kind of hardness modifier selected from the group consisting of crystalline cellulose, a D-mannitol granulated product, and isomalt into a composite granulated product obtained in the item 14.

Advantageous Effects of Invention

When an OD tablet is produced using the composite granulated product of the present invention, the OD tablet is excellent in disintegrability and has proper hardness.

In addition, when an OD tablet is produced using the composite granulated product of the present invention, the following OD tablet can be obtained: the OD tablet maintains its high hardness and disintegrability even under high temperature and increased humidity, and hence is excellent in storage stability.

DESCRIPTION OF EMBODIMENTS

[1] Composite Granulated Product

Figure 1:
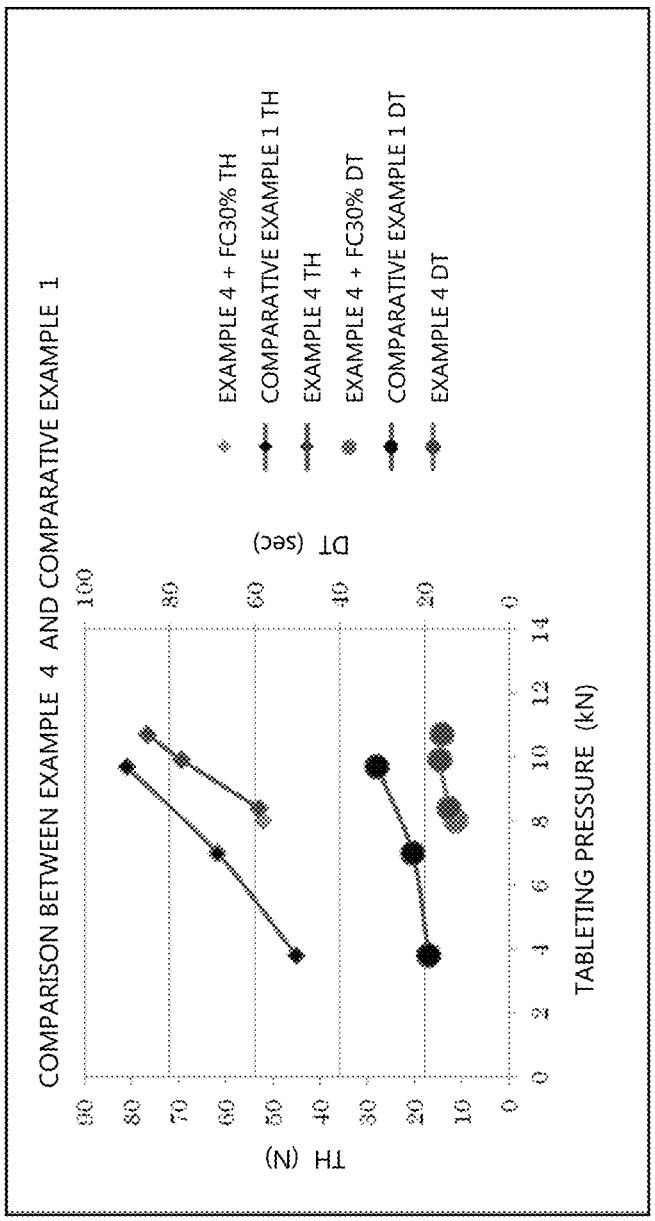
FIG. 1 is a graph for showing results of continuous tableting of Example 4 (Aero/XL-10) with a rotary tableting machine.

A composite granulated product of the present invention includes a sugar or a sugar alcohol, a swelling binder, a disintegrating agent, and a highly absorbent excipient.

The compositing of a composite granulated product is treatment involving the following steps:

(1) performing wet granulation by mixing a sugar or a sugar alcohol, a swelling binder, and a first disintegrating agent using a binding solution;

(2) performing granulation with addition of a highly absorbent excipient to a granulated product obtained in the step (1); and (3) performing granulation with addition of a second disintegrating agent to a granulated product obtained in the step (2).

The composite granulated product of the present invention is preferably used for an orally disintegrating tablet (OD tablet).

When an OD tablet is produced using the composite granulated product of the present invention, the following OD tablet can be obtained:

the OD tablet has high hardness and is also excellent in disintegrability, and the OD tablet maintains its high hardness and disintegrability even under high temperature and increased humidity, and hence is excellent in storage stability.

(1) Sugar or Sugar Alcohol

The sugar or the sugar alcohol is preferably at least one kind of component selected from the group consisting of D-mannitol, trehalose, xylitol, erythritol, lactose, and sucrose.

The average particle diameter of the sugar or the sugar alcohol is preferably from about 5 μm to about 100 μm, more preferably from about 10 μm to about 50 μm. A case in which the average particle diameter of the sugar or the sugar alcohol falls within the above-mentioned range is preferred because disintegrability and formability are improved, and mouth feeling is improved.

The average particle diameter of the sugar or the sugar alcohol is a volume-based particle diameter, and may be measured by a powder particle diameter measurement method using a laser diffraction method.

The content of the sugar or the sugar alcohol in the composite granulated product is preferably from about 70 mass % to about 98 mass %, more preferably from about 80 mass % to about 95 mass %. When the content of the sugar or the sugar alcohol falls within the above-mentioned range, hygroscopicity, stability of a formulation, formability, disintegrability, mouth feeling, and the like are improved.

(2) Swelling Binder

The swelling binder is preferably at least one kind of component selected from the group consisting of a polyvinyl alcohol-based polymer (PVA-based polymer), partially pregelatinized starch, hydroxypropyl cellulose (HPC), and crystalline cellulose.

For example, when the polyvinyl alcohol-based polymer is used, the size of granulated particles can be satisfactorily controlled. With regard to the size of the granulated particles, particles having an average particle diameter of about 200 μm or less are preferred.

The polyvinyl alcohol-based polymer (PVA-based polymer) is at least one kind of PVA-based polymer selected from polyvinyl alcohol (PVA) and derivatives thereof, and a PVA-based copolymer obtained by polymerizing at least one kind selected from PVA and derivatives thereof and at least one kind of polymerizable vinyl monomer.

The PVA-based polymer includes: PVA; derivatives of PVA (modified products of PVA); a PVA copolymer obtained by polymerizing PVA and another polymerizable vinyl monomer; a PVA-based copolymer obtained by polymerizing a derivative of PVA and another polymerizable vinyl monomer; and a PVA-based copolymer obtained by polymerizing PVA, a derivative of PVA, and another polymerizable vinyl monomer.

Herein, those polymers are collectively referred to as PVA-based polymer.

For the PVA and the derivatives thereof included in the PVA-based polymer, known ones may be used, and it is desired that commercially available products be easily available.

The polymerization degree of each of the PVA and the derivatives thereof is not particularly limited, and a polymerization degree optimal for concentration and viscosity that are suited to an intended use may be selected. The polymerization degree is, for example, from about 200 to about 2,000, preferably from about 300 to about 1,000.

In addition, it is preferred to use partially saponified PVA in which the saponification degree of each of the PVA and the derivatives thereof is preferably from about 60 mol % to about 100 mol %, more preferably from about 78 mol % to about 96 mol %, still more preferably from about 85 mol % to about 90 mol %.

Such saponified PVA may be manufactured by radically polymerizing vinyl acetate, and saponifying the obtained vinyl acetate as appropriate. The manufacture of desired PVA is achieved by appropriately controlling the polymerization degree and the saponification degree by a method known per se.

The PVA is a fully saponified product of polyvinyl acetate. As the derivatives of PVA, for example, there may be used various modified PVAs, such as amine-modified PVA, ethylene-modified PVA, and terminal thiol-modified PVA as well as an intermediately saponified product and partially saponified product of PVA.

As a commercially available derivative of PVA, there is given, for example, JP-05 manufactured by Japan VAM & Poval Co., Ltd. (partially saponified PVA, polymerization degree: 500, saponification degree: 88%).

In the PVA-based polymer, a polymerizable vinyl monomer may be bonded to or polymerized with part of a straight chain of each of the PVA and the derivatives thereof. In the PVA-based polymer, a polymerizable vinyl monomer may be bonded to part or all of hydroxy groups of the PVA and the derivatives thereof by an ester bond. The polymerizable vinyl monomer bonded to each of the PVA and the derivatives thereof may be further polymerized.

In the present invention, examples of the polymerizable vinyl monomer include:

(1) acrylic acid, methacrylic acid, fumaric acid, maleic acid, and itaconic acid;

(2) sodium salts, potassium salts, ammonium salts, and alkylamine salts of the monomers described above in (1); and (3) methyl methacrylate, methyl acrylate, ethyl methacrylate, ethyl acrylate, butyl methacrylate, butyl acrylate, isobutyl methacrylate, isobutyl acrylate, cyclohexyl methacrylate, cyclohexyl acrylate, 2-ethylhexyl methacrylate, 2-ethylhexyl acrylate, lauryl methacrylate, lauryl acrylate, stearyl methacrylate, stearyl acrylate, acrylonitrile, acrylamide, dimethylacrylamide, styrene, vinyl acetate, hydroxyethyl methacrylate, hydroxyethyl acrylate, an ester of polyethylene glycol and methacrylic acid, an ester of polyethylene glycol and acrylic acid, an ester of polypropylene glycol and methacrylic acid, an ester of polypropylene glycol and acrylic acid, N-vinylpyrrolidone, acryloylmorpholine, N,N-dimethylaminoethyl methacrylate, and methacryloyloxyethyl trimethylammonium chloride.

A preferred example of the polymerizable vinyl monomer is a compound represented by the following general formula (A):

$$H_2C=C(R^1)-COOR^2 \qquad (A)$$

where $R^1$ represents a hydrogen atom or a methyl group, and $R^2$ represents a hydrogen atom or an alkyl group having 1 to 4 carbon atoms.

The polymerizable vinyl monomers may be used alone or as a mixture thereof. When two or more kinds of polymerizable vinyl monomers are used as a mixture, the polymerizable vinyl monomers preferably include a compound in which $R^2$ represents a hydrogen atom and a compound in which $R^2$ represents an alkyl group having 1 to 4 carbon atoms among compounds represented by the general formula (A).

The use ratios of the compound in which $R^2$ in the general formula (A) represents a hydrogen atom and the compound in which $R^2$ represents an alkyl group having 1 to 4 carbon atoms in the PVA-based polymer, that is, with respect to 100 mass % of the total amount of at least one kind selected from PVA and derivatives thereof and the polymerizable vinyl monomers are preferably about 0.5 mass % to about 20 mass % of the compound in which $R^2$ represents a hydrogen atom and about 5 mass % to about 40 mass % of the compound in which $R^2$ represents an alkyl group having 1 to 4 carbon atoms, more preferably about 1.0 mass % to about 10 mass % of the compound in which $R^2$ represents a hydrogen atom and about 10 mass % to about 30 mass % of the compound in which $R^2$ represents an alkyl group having 1 to 4 carbon atoms.

A preferred combination of polymerizable vinyl monomers is combined use of at least one kind of the monomers described above in (1) and (2) and at least one kind of the monomers described above in (3). A more preferred combination of polymerizable vinyl monomers is combined use of acrylic acid or methacrylic acid and methyl methacrylate, that is, a combination of acrylic acid and methyl methacrylate, or a combination of methacrylic acid and methyl methacrylate.

A combination of acrylic acid and methyl methacrylate is particularly preferred. Further, the polymerizable vinyl monomers preferably include at least one kind selected from the group consisting of acrylic acid and methyl methacrylate, and it is particularly preferred that only acrylic acid and methyl methacrylate be used as the polymerizable vinyl monomers.

The use ratios of acrylic acid and methyl methacrylate in the PVA-based polymer, that is, with respect to 100 mass % of the total amount of at least one kind selected from PVA and derivatives thereof and the polymerizable vinyl monomer are preferably about 0.5 mass % to about 20 mass % of acrylic acid and about 5 mass % to about 40 mass % of methyl methacrylate, more preferably about 1.0 mass % to about 10 mass % of at least one kind selected from the group consisting of acrylic acid and methacrylic acid and about 10 mass % to about 30 mass % of methyl methacrylate.

In particular, a polyvinyl alcohol-based copolymer obtained by polymerizing 0.5 wt % to 20 wt % of acrylic acid, 5 to 40 wt % of methyl methacrylate, and 40 wt % to 94.5 wt % of PVA with respect to the total amount of acrylic acid, methyl methacrylate, and PVA is preferred, and a PVA-based copolymer obtained by polymerizing 2.5 wt % to 5.0 wt % of acrylic acid, 15 to 25 wt % of methyl methacrylate, and 20 wt % to 70 wt % of PVA is more preferred.

A copolymer obtained by polymerizing acrylic acid and methyl methacrylate in the presence of PVA is commercially available, and is available under the name of POVACOAT from Daido Chemical Corporation. In the present invention, the commercially available product may be used.

In the PVA-based polymer, a polymerizable vinyl monomer may be bonded to or polymerized with part of a straight chain of each of the PVA and the derivatives thereof. In the PVA-based polymer, a polymerizable vinyl monomer may be bonded to part or all of hydroxy groups of the PVA and the derivatives thereof by an ester bond. The polymerizable vinyl monomer bonded to each of the PVA and the derivatives thereof may be further polymerized.

An example of the PVA-based polymer is a polymer obtained by graft-polymerizing a polymerizable vinyl monomer to PVA (chain). Such polymer is preferably a PVA-based polymer obtained by graft-polymerizing at least one kind selected from the group consisting of acrylic acid and methyl methacrylate to at least one kind selected from PVA and derivatives thereof.

The weight-average molecular weight of the PVA-based polymer is preferably from about 10,000 to about 500,000, more preferably from about 35,000 to about 300,000.

For the PVA-based polymer, a commercially available product may be used. When the commercially available product is used, for example, POVACOAT (trademark:

manufactured by Daido Chemical Corporation) may be used. POVACOAT (polyvinyl alcohol/acrylic acid/methyl methacrylate copolymer) is a synthetic polymer obtained by copolymerizing partially saponified polyvinyl alcohol with acrylic acid and methyl methacrylate. The PVA-based polymer is represented by the following structural formula as a general formula.

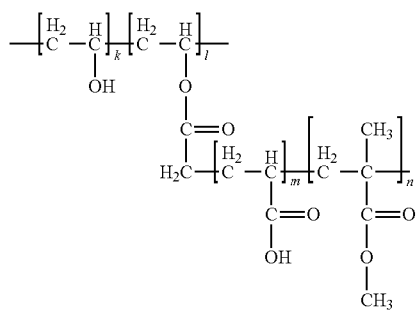

[Chem 1]

In the structural formula, about 60% to about 85% of k, about 5% to about 20% of l, about 0.5% to about 15% of m, and about 0.3% to about 25% of n are preferably included in 100% of the sum of k, l, m, and n.

The average molecular weight (Mw) of such PVA-based polymer is preferably from about 25,000 to about 200,000.

The average polymerization degree of such PVA-based polymer is preferably from about 300 to about 1,500.

The labeled viscosity of such PVA-based polymer is preferably from about 5.5 mPA·s to about 20 mPA·s.

For example, POVACOAT Type F having an average molecular weight (Mw) of about 40,000, or POVACOAT Type MP, POVACOAT Type FM, and POVACOAT Type SP each having an average molecular weight (Mw) of about 40,000 but having different average particle diameters, or POVACOAT Type R having an average molecular weight (Mw) of about 200,000 may be used.

POVACOAT Type MP is a pulverized product of POVACOAT Type F (average particle diameter: about 125 μm).

POVACOAT Type FM is a pulverized product of Type F (average particle diameter: about 30 μm), and is a frozen and pulverized product.

POVACOAT Type SP is a pulverized product prepared by pulse combustion drying (average particle diameter: about 20 μm).

The PVA and the derivatives thereof may be used alone or as a mixture thereof.

Other than the PVA-based polymer, the swelling binder is preferably partially pregelatinized starch, hydroxypropyl cellulose (HPC), crystalline cellulose, or the like. HPC is more preferably low-substituted HPC (L-HPC).

As another binder, for example, polyvinylether, polyvinylpyrrolidone, hydroxypropyl methylcellulose, hydroxyethyl cellulose, carboxyvinyl polymer, cellulose powder, crystalline cellulose, carmellose sodium, methyl cellulose, ethyl cellulose, potassium phosphate, gum arabic powder, pullulan, pectin, dextrin, hydroxypropyl starch, gelatin, xanthan gum, carrageenan, tragacanth, tragacanth powder, polyethylene glycol, carboxymethylcellulose sodium, methyl cellulose, or sodium alginate may be used in combination with the above-mentioned swelling binder.

The average particle diameter of the swelling binder is preferably from about 10 μm to about 200 μm, more preferably from about 15 μm to about 150 μm. When the average particle diameter of the swelling binder falls within the above-mentioned range, the swelling binder shows proper swellability and solubility to improve fluidity, disintegrability, formability, and the like.

When the swelling binder has the preferred average particle diameter, an optimal composite granulated product to be used for an OD tablet can be prepared. The average particle diameter is a volume-based particle diameter, and may be measured by a powder particle diameter measurement method using a laser diffraction method.

The content of the swelling binder in the composite granulated product is preferably from about 0.1 mass % to about 25 mass %, more preferably from about 0.3 mass % to about 20 mass %. When the content of the swelling binder falls within the above-mentioned range, hygroscopicity, stability of a formulation, binding property, disintegrability, and the like are improved.

(3) Disintegrating Agent

The disintegrating agent is preferably at least one kind of component selected from the group consisting of hydroxypropyl cellulose (HPC, preferably low-substituted HPC), crospovidone, starch (preferably starch (soluble)), croscarmellose sodium, carmellose calcium, carmellose, and partially pregelatinized starch.

The hydroxypropyl cellulose contains cellulose as a basic backbone, and is preferably low-substituted hydroxypropyl cellulose (L-HPC) obtained by introducing a small amount of hydroxypropoxy groups into the basic backbone. The L-HPC is a water-insoluble polymer and has a characteristic of swelling by absorbing water, and its degree of hydroxypropoxy substitution is preferably from about 5 mass % to about 16 mass %, more preferably from about 5 mass % to about 9 mass %.

When the degree of hydroxypropoxy substitution falls within the above-mentioned range, swellability after water absorption, disintegrability, binding property, water solubility, and the like are improved. When the L-HPC is used, the stability of a tablet (preferably an OD tablet) is improved. In addition, the L-HPC has good compatibility with the PVA-based polymer, and hence improves the stability of a tablet (preferably an OD tablet).

The use of crospovidone, starch (corn starch or the like), croscarmellose sodium, carmellose calcium, carmellose, partially pregelatinized starch, or the like provides the following effect: the disintegrability of the prepared OD tablet is excellent.

As another disintegrating agent, starch, dry starch, carboxymethyl starch sodium, sodium starch glycolate, agar powder, sodium hydrogen carbonate, calcium carbonate, or the like may be used in combination with the above-mentioned disintegrating agent.

The average particle diameter of the disintegrating agent is preferably from about 2 μm to about 100 μm, more preferably from about 10 μm to about 80 μm. When the average particle diameter of the disintegrating agent falls within the above-mentioned range, water absorption swellability, disintegrability, binding property, and the like are improved.

The average particle diameter is a volume-based particle diameter, and may be measured by a powder particle diameter measurement method using a laser diffraction method.

The content of the disintegrating agent in the composite granulated product is preferably from about 2 mass % to about 30 mass %, more preferably from about 5 mass % to about 20 mass %. When the content of the disintegrating agent falls within the above-mentioned range, disintegrability and the like are improved.

(4) Highly Absorbent Excipient

The highly absorbent excipient is preferably at least one kind of component selected from the group consisting of light anhydrous silicic acid, hydrated silicon dioxide, calcium silicate, and magnesium aluminometasilicate. When any of those components is used, the average particle diameter of the composite granulated product can be made sharper.

As another excipient, for example, allose, talose, gulose, glucose, altrose, mannose, galactose, idose, ribose, lyxose, xylose, arabinose, apiose, erythrose, threose, glyceraldehyde, sedoheptulose, coriose, psicose, fructose, sorbose, tagatose, ribulose, xylulose, erythrulose, dihydroxyacetone, isotrehalose, kojibiose, sophorose, nigerose, laminaribiose, maltose, cellobiose, isomaltose, gentiobiose, lactose, sucrose, sodium chloride, starch, reduced palatinose, carbonates, such as calcium carbonate, kaolin, silicic acid, methyl cellulose, sodium alginate, gum arabic, talc, phosphates, such as potassium hydrogen phosphate, calcium hydrogen phosphate, sodium hydrogen phosphate, dipotassium phosphate, disodium phosphate, potassium dihydrogen phosphate, calcium dihydrogen phosphate, and sodium dihydrogen phosphate, calcium sulfate, calcium lactate, oligosaccharides, such as lactulose, raffinose, and lactosucrose, magnesium aluminosilicate, calcium silicate, and magnesium silicate may be used in combination with the above-mentioned highly absorbent excipient.

The average particle diameter of the highly absorbent excipient is preferably from about 5 μm to about 100 μm, more preferably from about 10 μm to about 60 μm. When the average particle diameter of the disintegrating agent falls within the above-mentioned range, water absorption swellability, disintegrability, binding property, and the like are improved.

The average particle diameter is a volume-based particle diameter, and may be measured by a powder particle diameter measurement method using a laser diffraction method.

The content of the highly absorbent excipient in the composite granulated product is preferably from about 3 mass % to about 20 mass %, more preferably from about 5 mass % to about 15 mass %. When the content of the highly absorbent excipient falls within the above-mentioned range, the average particle diameter of the composite granulated product can be made sharper.

The present invention is directed to the composite granulated product including the sugar or the sugar alcohol, the swelling binder, the disintegrating agent, and the highly absorbent excipient.

The compositing of a composite granulated product is treatment involving the following steps:

(1) performing wet granulation by mixing a sugar or a sugar alcohol, a swelling binder, and a first disintegrating agent using a binding solution;

(2) performing granulation with addition of a highly absorbent excipient to a granulated product obtained in the step (1); and (3) performing granulation with addition of a second disintegrating agent to a granulated product obtained in the step (2).

(5) Hardness Modifier and Granule for Tableting

A hardness modifier is preferably added to the composite granulated product including the above-mentioned components. Through the addition of the hardness modifier to the composite granulated product, a granule for tableting may be prepared.

The hardness modifier is an additive for increasing hardness without sacrificing disintegration time, by being further added to the composite granulated product including the above-mentioned components.

The hardness modifier is preferably at least one kind of hardness modifier selected from the group consisting of crystalline cellulose, a D-mannitol granulated product, and isomalt. D-mannitol is preferably a D-mannitol granulated product prepared by spray drying or the like. Isomalt is a sugar alcohol using sucrose as a raw material.

When any of those components is used, the hardness of a prepared OD tablet can be increased.

The average particle diameter of the hardness modifier is preferably from about 10 μm to about 200 μm, more preferably from about 15 μm to about 150 μm. When the average particle diameter of the hardness modifier falls within the above-mentioned range, the prepared OD tablet shows proper hardness, and fluidity, disintegrability, formability, and the like are improved.

When the hardness modifier has the preferred average particle diameter, an optimal composite granulated product to be used for an OD tablet can be prepared. The average particle diameter is a volume-based particle diameter, and may be measured by a powder particle diameter measurement method using a laser diffraction method.

The content of the hardness modifier in the composite granulated product is preferably from about 0.1 mass % to about 25 mass %, more preferably from about 0.3 mass % to about 20 mass %. When the content of the hardness modifier falls within the above-mentioned range, the following effect is obtained in the prepared OD tablet: its hardness is increased without sacrificing its disintegration time.

[2] Tablet Containing Composite Granulated Product

A tablet of the present invention contains a medicinal component, functional particles, and the like in addition to the above-mentioned composite granulated product.

(1) Composite Granulated Product

The above-mentioned composite granulated product may be used.

The average particle diameter of the composite granulated product is preferably from about 50 μm to about 250 μm, more preferably from about 60 μm to about 200 μm. When the average particle diameter of the composite granulated product falls within the above-mentioned range, the prepared OD tablet shows proper hardness, and is improved in water absorption swellability, disintegrability, binding property, and the like.

The average particle diameter is a volume-based particle diameter, and may be measured by a powder particle diameter measurement method using a laser diffraction method.

The content of the composite granulated product in the tablet is preferably from about 0.1 mass % to about 90 mass %, more preferably from about 1 mass % to about 80 mass %. When the content of the composite granulated product falls within the above-mentioned range, hygroscopicity, stability of a formulation, binding property, disintegrability, and the like are improved.

(2) Medicinal Component

The medicinal component may be selected from a wide range of fields, such as pharmaceutical compounds (pharmaceutical compounds including animal drugs), medical materials (medical materials including regenerative medical materials, such as artificial skin), pesticide compounds, fertilizers, cosmetics, perfumes, food materials, feeds, germicides, fungicides, insect repellents, insecticides, corrosion inhibitors, absorbents, and coating materials.

The following components are preferred as the pharmaceutical compounds.

It is preferred that at least one kind of component selected from these components be used.

(1) Sympathomimetic Drugs

Adrenaline, noradrenaline, etilefrine, naphazoline, phenylephrine, methoxamine, midodrine, isoprenaline, isoproterenol, dobutamine, denopamine, trimetoquinol, salbutamol, terbutaline, tulobuterol, fenoterol, procaterol, clenbuterol, salmeterol, mabuterol, ritodrine, isoxsuprine, tyramine, amphetamine, methamphetamine, ephedrine, methylephedrine, dopamine, docarpamine, amezinium, or salts thereof, and the like.

(2) Sympatholytic Drugs

Ergotamine, ergometrine, phentolamine, tolazoline, prazosin, bunazosin, terazosin, urapidil, doxazosin, tamsulosin, silodosin, naftopidil, alprenolol, oxprenolol, propranolol, bufetolol, pindolol, carteolol, timolol, nadolol, nipradilol, atenolol, metoprolol, bisoprolol, labetalol, amosulalol, arotinolol, carvedilol, reserpine, guanethidine, α-methyldopa, clonidine, guanabenz, or salts thereof, and the like.

(3) Parasympathomimetic Drugs

Acetylcholine, bethanechol, carbachol, methacholine, pilocarpine, muscarine, physostiymine, neostigmine, distiymine, pyridostiymine, ambenonium, edrophonium, pilocarpine, carpronium, cevimeline, or salts thereof, and the like.

(4) Parasympatholytic Drugs

Homatropine, tropicamide, cyclopentolate, propantheline, butylscopolamine, mepenzolate, prifinium, pirenzepine, ipratropium, oxitropium, piperidolate, propiverine, oxybutynin, trihexyphenidyl, biperiden, piroheptine, mazaticol, profenamine, metixene, or salts thereof, and the like.

(5) Autonomic Ganglionic Blockers

Hexamethonium, trimethaphan, nicotine, or salts thereof, and the like.

(6) Local Anesthetics

Cocaine, procaine, oxybuprocaine, tetracaine, ethyl aminobenzoate, lidocaine, dibucaine, mepivacaine, oxethazaine, xylocaine, or salts thereof, and the like.

(7) Muscle Relaxants

Tubocurarine, pancuronium, vecuronium, suxamethonium, dantrolene, pridinol, mephenesin, chlorzoxazone, phenprobamate, methocarbamol, chlormezanone, pridinol mesylate, afloqualone, chlorphenesin, tizanidine, tolperisone, eperisone, baclofen, or salts thereof, and the like.

(8) Intravenous Anesthetics

Thiopental, thiamylal, propofol, midazolam, droperidol, ketamine, or salts thereof, and the like.

(9) Hypnotics

Flurazepam, haloxazolam, quazepam, nitrazepam, flunitrazepam, estazolam, nimetazepam, brotizolam, rilmazafone, lormetazepam, triazolam, zolpidem, zopiclone, bromovalerylurea, barbital, phenobarbital, amobarbital, secobarbital, pentobarbital, thiopental, thiamylal, ramelteon, or salts thereof, and the like.

(10) Analgesics and Antitussives

Morphine, codeine, papaverine, noscapine, dihydrocodeine, oxycodone, diacetylmorphine, pethidine, methadone, levorphanol, fentanyl, remifentanil, pentazocine, butorphanol, buprenorphine, naloxone, levallorphan, dextromethorphan, tipepidine, guaifenesin, pentoxyverine, benzonatate, oxymorphone, cloperastine, or salts thereof, and the like.

(11) Anti-Epileptics

Phenobarbital, primidone, phenytoin, carbamazepine, ethosuximide, trimethadione, diazepam, clonazepam, nitrazepam, valproic acid, gabapentin, sultiame, zonisamide, or salts thereof, and the like.

(12) Anti-Parkinson Drugs

Levodopa, carbidopa, benserazide, entacapone, bromocriptine, pergolide, cabergoline, talipexole, pramipexole, amantadine, selegiline, trihexyphenidyl, biperiden, profenamine, piroheptine, metixene, mazaticol, droxidopa, or salts thereof, and the like.

(13) Anti-Alzheimer Drugs

Donepezil, galantamine, rivastiymine, memantine, or salts thereof, and the like.

(14) Schizophrenia Therapeutic Agents

Chlorpromazine, fluphenazine, thioridazine, haloperidol, bromperidol, spiperone, haloperidol decanoate, sulpiride, risperidone, perospirone, olanzapine, quetiapine, clozapine, aripiprazole, prochlorperazine, trifluoperazine, zotepine, or salts thereof, and the like.

(15) Anxiolytics

Etizolam, diazepam, oxazolam, ethyl loflazepate, clotiazepam, lorazepam, tandospirone, hydroxyzine, oxazepam, medazepam, temazepam, fludiazepam, meprobamate, chlordiazepoxide, or salts thereof, and the like.

(16) Antidepressants

Imipramine, clomipramine, amitriptyline, nortriptyline, desipramine, amoxapine, maprotiline, mianserin, setiptiline, trazodone, fluvoxamine, paroxetine, sertraline, milnacipran, duloxetine, mirtazapine, noxiptiline, phenelzine, or salts thereof, and the like.

(17) Vertigo Therapeutic Agents

Dimenhydrinate, difenidol, betahistine, or salts thereof, and the like.

(18) Cardiotonics

Digitoxin, digoxin, metildigoxin, deslanoside, dobutamine, denopamine, dopamine, docarpamine, colforsin daropate, aminophylline, milrinone, olprinone, pimobendan, bucladesine, trans-n-oxocamphor, terephyllol, etilefrine, or salts thereof, and the like.

(19) Anti-Arrhythmics

Quinidine, procainamide, disopyramide, ajmaline, cibenzoline, pirmenol, lidocaine, mexiletine, aprindine, phenytoin, propafenone, flecainide, pilsicainide, propranolol, alprenolol, bufetolol, oxprenolol, pindolol, carteolol, nadolol, atenolol, acebutolol, metoprolol, bisoprolol, amiodarone, sotalol, nifekalant, verapamil, diltiazem, bepridil, or salts thereof, and
the like.

(20) Vasodilator and Hypertension Therapeutic Agents

Nitroglycerin, isosorbide nitrate, nicorandil, nifedipine, amlodipine, nitrendipine, nicardipine, felodipine, cilnidipine, manidipine, diltiazem, captopril, lisinopril, alacepril, enalapril, temocapril, imidapril, losartan, valsartan, candesartan cilexetil, olmesartan medoxomil, azilsartan, aliskiren, hydralazine, bosentan, ethyl icosapentate, nicomol, niceritrol, isoxsuprine, tolazoline, hexobendine, bamethan, nilvadipine, trapidil, dilazep, beraprost, alprostadil, or salts thereof, and the like.

(21) Hypotension Therapeutic Agents

Phenylephrine, midodrine, methoxamine, etilefrine, ephedrine, dihydroergotamine, amezinium, or salts thereof, and
the like.

(22) Diuretics

Acetazolamide, furosemide, bumetanide, torsemide, azosemide, piretanide, hydrochlorothiazide, trichlormethiazide, spironolactone, canrenoic acid, eplerenone, triamterene, isosorbide, methyclothiazide, hydroflumethiazide, ethiazide, cyclopenthiazide, chlorothiazide, ethacrynic acid, or salts thereof, and the like.

(23) Dysuria Therapeutic Agents

Tamsulosin, silodosin, naftopidil, prazosin, terazosin, urapidil, bethanechol, neostiymine, distigmine, oxendolone, chlormadinone acetate, allylestrenol, gestonorone caproate, or salts thereof, and the like.

(24) Pollakiuria Therapeutic Agents

Propiverine, oxybutynin, solifenacin, imidafenacin, tolterodine, imipramine, clomipramine, amitriptyline, clenbuterol, mirabegron, flavoxate, terodiline, or salts thereof, and the like.

(25) Expectorants

Bromhexine, acetylcysteine, ethylcysteine, methylcysteine, carbocysteine, ambroxol, senega, polygala root, platycodon root, chlophedianol, picoperidamine, or salts thereof, and the like.

(26) Bronchial Asthma Therapeutic Agents

Theophylline, aminophylline, ipratropium, oxitropium, beclomethasone propionate, fluticasone propionate, dexamethasone, prednisolone, budesonide, trimetoquinol, salbutamol, terbutaline, procaterol, salmeterol, fenoterol, tulobuterol, mabuterol, clenbuterol, formoterol, indacaterol, methoxyphenamine, or salts thereof, and the like.

(27) Gastric or Duodenal Ulcer Therapeutic Agents

Pirenzepine, propantheline, butylscopolamine, cimetidine, ranitidine, famotidine, nizatidine, roxatidine acetate, proglumide, oxethazaine, omeprazole, lansoprazole, rabeprazole, sucralfate, teprenone, cetraxate, rebamipide, gefarnate, ecabet, azulene, sulpiride, misoprostol, enprostil, irsogladine, roxatidine acetate, magnesium oxide, synthetic aluminum silicate, or salts thereof, and the like.

(28) Stomachics and Cathartics

Metoclopramide, domperidone, mosapride, sennoside, picosulfate, bisacodyl, gentian, swertia herb, coptis rhizome, phellodendron bark, fennel, cinnamon bark, ginger, Japanese zanthoxylum peel, carmellose, dioctyl sodium sulfosuccinate, lactulose, magnesium oxide, magnesium sulfate, magnesium hydroxide, or salts thereof, and the like.

(29) Antidiarrheals

Atropine, loperamide, trimebutine, opium, mepenzolate, albumin tannate, bismuth subnitrate, natural aluminum silicate, berberine, nalidixic acid, or salts thereof, and the like.

(30) Antiemetics

Chlorpromazine, sulpiride, domperidone, metoclopramide, granisetron, ondansetron, azasetron, oxethazaine, dimenhydrinate, promethazine, aprepitant, apomorphine, ipecac (emetine or cephaeline), or salts thereof, and the like.

(31) Liver or Pancreas Therapeutic Agents

Interferon preparations, lamivudine, glycyrrhizin, protoporphyrin, saikosaponin, lactulose, dehydrocholic acid, ursodeoxycholic acid, flopropione, chenodeoxycholic acid, nafamostat, ulinastatin, gabexate, camostat, trepibutone, or salts thereof, and the like.

(32) Drugs for Genitalia

Sildenafil, vardenafil, tadalafil, udenafil, mirodenafil, ergometrine, methylergometrine, oxytocin, dinoprostone, dinoprost, gemeprost, ritodrine, isoxsuprine, piperidolate, or salts thereof, and the like.

(33) Glaucoma Therapeutic Agents

Pilocarpine, distiymine, latanoprost, isopropyl unoprostone, bunazosin, acetazolamide, dorzolamide, timolol, carteolol, levobunolol, nipradilol, dipivefrine, or salts thereof, and the like.

(34) Ophthalmic Diagnostic Agents (Miotic Agents or Mydriatic Agents)

Phenylephrine, homatropine, tropicamide, cyclopentolate, pilocarpine, or salts thereof, and the like.

(35) Skin Disease Therapeutic Agents

Tacalcitol, etretinate, urea, methoxsalen, lysozyme, alprostadil, alprostadil alfadex, tretinoin tocoferil, trafermin, or salts thereof, and the like.

(36) Hormonal Drugs, Hormone Replacement Drugs, Anti-Hormone Drugs, and Autacoids Corticotropin releasing hormone, thyrotropin-releasing hormone, gonadotropin-releasing hormone, luteinizing hormone-releasing hormone, growth hormone-releasing hormone, prolactin-releasing hormone, prolactin-release-inhibiting hormone, adrenocorticotropic hormone, thyroid-stimulating hormone, follicle-stimulating hormone, luteinizing hormone, growth hormone, corticorelin, protirelin, gonadorelin, buserelin, goserelin, nafarelin, leuprorelin, cetrorelix, ganirelix, somatorelin, terguride, somatostatin, octreotide, prolactin, somatropin, oxytocin, vasopressin, desmopressin, thyroxin, triiodothyronine, calcitonin, parathormone, liothyronine, levothyroxine, thiamazole, propylthiouracil, hydrocortisone, prednisolone, pregnenolone, methylprednisolone, dexamethasone, betamethasone, triamcinolone, triamcinolone acetonide, fluocinolone acetonide, metyrapone, trilostane, testosterone, methyltestosterone, metenolone, nandrolone, chlormadinone, allylestrenol, oxendolone, flutamide, bicalutamide, finasteride, estradiol, estriol, ethinylestradiol, clomiphene, tamoxifen, toremifene, mepitiostane, anastrozole, exemestane, progesterone, medroxyprogesterone, dydrogesterone, norethisterone, danazol, desogestrel, norgestrel, levonorgestrel, human chorionic gonadotropin, gastrin, cholecystokinin, secretin, glucagon, insulin, melatonin, gastric inhibitory peptide, adrenaline, noradrenaline, aldosterone, dopamine, desoxycorticosterone, arachidonic acid, leukotriene A4, leukotriene B4, leukotriene C4, leukotriene D4, leukotriene E4, prostaglandin G2, prostaglandin H2, prostaglandin 12, prostaglandin E2, prostaglandin D2, prostaglandin F2α, thromboxane A2, thromboxane B2, serotonin, histamine, angiotensin, bradykinin, renin, endothelin, γ-aminobutyric acid, various cytokines, phosphatidylcholine, phosphatidylinositol, platelet-activating factor (PAF), phosphatidylinositol bisphosphate (PIP2), galactocerebroside, ganglioside, gestonorone caproate, hexestrol, erythropoietin, or derivatives thereof, and the like.

(37) Diabetes Therapeutic Agents

Insulin preparations, tolbutamide, acetohexamide, chlorpropamide, gliclazide, glibenclamide, glimepiride, nateglinide, mitiglinide, metformin, buformin, pioglitazone, acarbose, voglibose, miglitol, sitagliptin, vildagliptin, alogliptin, liraglutide, exenatide, epalrestat, or salts thereof, and the like.

(38) Antilipemics

Pravastatin, simvastatin, fluvastatin, atorvastatin, cholestyramine, colestimide, ezetimibe, γ-oryzanol, soy sterol, probucol, clofibrate, bezafibrate, fenofibrate, nicomol, niceritrol, dextran sulfate, ethyl icosapentate, ethyl 2-chloro-3-[4-(2-methyl-2-phenylpropoxy)phenyl]propanoate [Chem. Pharm. Bull., 38, 2792-2796 (1990)], clinofibrate, soy sterol, or salts thereof, and the like.

(39) Hyperuricemia and Gout Therapeutic Agents

Colchicine, allopurinol, febuxostat, probenecid, benzbromarone, bucolome, or salts thereof, and the like.

(40) Osteoporosis Therapeutic Agents

Estradiol, raloxifene, elcatonin, salmon calcitonin, ipriflavone, calcitriol, α-calcidol, menatetrenone, etidronic acid, alendronic acid, risedronic acid, teriparatide, or salts thereof, and the like.

(41) Hemostatics

Phytonadione, menatetrenone, thrombin, hemocoagulase, tranexamic acid, carbazochrome, or salts thereof, and the like.

(42) Antithrombogenic Drugs

Heparin, dalteparin, danaparoid, warfarin, argatroban, urokinase, alteplase, monteplase, aspirin, ozagrel, ethyl icosapentate, sarpogrelate, ticlopidine, clopidogrel, beraprost, cilostazol, dipyridamole, or salts thereof, and the like.

(43) Hematinic Drugs

Cideferron, cyanocobalamin, hydroxocobalamin, mecobalamin, folic acid, metenolone, nandrolone, erythropoietin preparations, pyridoxal phosphate, pyridoxine, filgrastim, lenograstim, nartograstim, mirimostim, or salts thereof, and the like.

(44) Non-Steroidal Anti-Inflammatory Drugs (NSAIDs)

Aspirin, salicylamide, indometacin, indometacin farnesil, acemetacin, sulindac, piroxicam, ampiroxicam, tenoxicam, meloxicam, diclofenac, felbinac, ibuprofen, naproxen, loxoprofen, flurbiprofen, flurbiprofen axetil, ketoprofen, mefenamic acid, flufenamic acid, etodolac, celecoxib, tiaramide, epirizole, salicylic acid, sulpyrine, aminopyrine, phenacetin, phenylbutazone, ketophenylbutazone, benzydamine, mepirizole, tinoridine, isopropylantipyrine, sazapyrine, clofezone, or salts thereof, and the like.

(45) Immunosuppressants

Cyclosporine, tacrolimus, azathioprine, mizoribine, mycophenolate mofetil, cyclophosphamide, gusperimus, muromonab-CD3, basiliximab, or salts thereof, and the like.

(46) Rheumatoid Arthritis Therapeutic Agents

Gold thiomalate, auranofin, D-penicillamine, bucillamine, methotrexate, leflunomide, actarit, lobenzarit, salazosulfapyridine, or salts thereof, and the like.

(47) Anti-Allergic Drugs

Cromoglicic acid, tranilast, pemirolast, amlexanox, diphenhydramine, chlorpheniramine, clemastine, promethazine, cyproheptadine, azelastine, ketotifen, oxatomide, mequitazine, epinastine, fexofenadine, cetirizine, ebastine, olopatadine, loratadine, ozagrel, seratrodast, ramatroban, pranlukast, montelukast, zafirlukast, ibudilast, suplatast, tripelennamine, methdilazine, clemizole, diphenylpyraline, alimemazine, or salts thereof, and the like.

(48) Antibiotics

Benzylpenicillin, sultamicillin, phenethicillin, cloxacillin, ampicillin, bacampicillin, amoxicillin, piperacillin, cephalothin, cefazolin, cefalexin, cefaclor, cefotiam, cefuroxime axetil, cefsulodin, cefotaxime, cefmenoxime, ceftizoxime, cefoperazone, ceftriaxone, cefuzonam, ceftazidime, cefodizime, cefixime, cefdinir, cefpodoxime proxetil, cefditoren pivoxil, cefcapene pivoxil, cefepime, cefpirome, cefozopran, cefotaxime, cefmetazole, cefbuperazone, cefminox, latamoxef, flomoxef, aztreonam, tebipenem pivoxil, aztreonam, carumonam, vancomycin, reonam, imipenem, panipenem, meropenem, faropenem, biapenem, doripenem, teicoplanin, fosfomycin, streptomycin, kanamycin, tobramycin, fradiomycin, gentamycin, amikacin, arbekacin, spectinomycin, chloramphenicol, erythromycin, clarithromycin, roxithromycin, azithromycin, spiramycin, josamycin, midecamycin, acetylspiramycin, rokitamycin, tetracycline, minocycline, doxycycline, lincomycin, clindamycin, mupirocin, linezolid, polymyxin B, colistin, sulfamethoxazole, salazosulfapyridine, sulfadimethoxine, sulfadoxine, nalidixic acid, norfloxacin, moxifloxacin, garenoxacin, sitafloxacin, ofloxacin, enoxacin, ciprofloxacin, levofloxacin, lomefloxacin, tosufloxacin, sparfloxacin, gatifloxacin, prulifloxacin, pazufloxacin, sulbactam, tazobactam, quinupristin, dalfopristin, clavulanic acid, pivmecillinam, telithromycin, isoniazid, pyrazinamide, rifampicin, ethambutol, p-aminosalicylic acid, diaphenylsulfone, clofazimine, lankacidins [J. AntiBiotics, 38, 877-885 (1985)], pipemidic acid trihydrate, dibekacin, kanendomycin, lividomycin, dibekacin, sisomicin, oxytetracycline, rolitetracycline, ticarcillin, cephaloridine, cefotiam hexetil, cefsulodin, moxalactam, thienamycin, or salts thereof, and the like.

(49) Antiprotozoals and Antiparasitics

Quinine, mefloquine, sulfadoxine, pyrimethamine, metronidazole, tinidazole, spiramycin acetate, pentamidine, santonin, pyrantel, mebendazole, ivermectin, diethylcarbamazine, praziquantel, albendazole, levamisole, or salts thereof, and the like.

(50) Antifungal Drugs

Amphotericin B, nystatin, itraconazole, clotrimazole, ketoconazole, fluconazole, miconazole, micafungin, terbinafine, butenafine, flucytosine, griseofulvin, or salts thereof, and the like.

(51) Antiviral Drugs

Acyclovir, valaciclovir, ganciclovir, vidarabine, foscarnet, amantadine, oseltamivir, zanamivir, laninamivir octanoate, peramivir, zidovudine, didanosine, lamivudine, sanilvudine, abacavir, nevirapine, efavirenz, delavirdine, saquinavir, ritonavir, indinavir, nelfinavir, fosamprenavir, lopinavir, raltegravir, interferon preparations, ribavirin, or salts thereof, and the like.

(52) Antineoplastic Drugs

Cyclophosphamide, ifosfamide, busulfan, thiotepa, melphalan, nimustine, ranimustine, lomustine, carmustine, mercaptopurine, fludarabine, fluorouracil, tegafur, doxifluridine, capecitabine, cytarabine, cytarabine ocfosfate, enocitabine, gemcitabine, methotrexate, folinate, levofolinate, doxorubicin, daunorubicin, epirubicin, adriamycin, idarubicin, bleomycin, mitomycin C, actinomycin D, vincristine, vinblastine, vindesine, vinorelbine, paclitaxel, docetaxel, irinotecan, nogitecan, etoposide, tamoxifen, mepitiostane, toremifene, anastrozole, letrozole, flutamide, chlormadinone acetate, medroxyprogesterone acetate, leuprorelin, goserelin, cisplatin, carboplatin, nedaplatin, oxaliplatin, L-asparaginase, hydroxycarbamide, dacarbazine, temozolomide, procarbazine, melphalan, cladribine, nelarabine, fludarabine, pemetrexed, pentostatin, eribulin, sobuzoxane, vinorelbine, vindesine, aclarubicin, amrubicin, idarubicin, epirubicin, zinostatin stimalamer, pirarubicin, pepromycin, mitoxantrone, exemestane, estramustine, mitotane, mepitiostane, ubenimex, lentinan, thalidomide, neocarzinostatin, cytosine arabinoside, tetrahydrofuryl-5-fluorouracil, picibanil, lentinan, bestatin, mitoxantrone, aminoglutethimide, or salts thereof, and the like.

(53) Molecular Target Therapeutic Agents (Low-Molecular-Weight Compounds)

Imatinib, gefitinib, erlotinib, dasatinib, lapatinib, nilotinib, sorafenib, sunitinib, crizotinib, axitinib, temsirolimus, everolimus, bortezomib, tamibarotene, tretinoin, vandetanib, and the like.

(54) Diagnostic Agents and Test Agents

Amidotrizoic acid, meglumine, iotalamic acid, meglumine iothalamate, meglumine iotroxate, iopromide, iomeprol, iopamidol, iohexol, ioxilan, iotrolan, iodixanol, gadodiamide, sulfobromophthalein, indocyanine green, indigo carmine, p-aminohippuric acid, phenolsulfonphthalein, inulin, creatinine, Evans blue, tetragastrin, tuberculin, edrophonium, o-tolidine, or salts thereof, and the like.

(55) Antidotes and Antagonists

Dimercaprol, edetic acid, D-penicillamine, trientine, deferoxamine, amyl nitrite, thiosulfuric acid, pralidoxime, atropine, nalorphine, naloxone, levallorphan, flumazenil, dimorpholamine, folinate, protamine, phytonadione, acetylcysteine, mesna, dimesna, pyridoxine, pyridoxal phosphate, disulfiram, cyanamide, or salts thereof, and the like.

(56) Crude Drugs

Asinus gelatin, clematis root, Artemisia capillaris flower, fennel, lindera root, corydalis tuber, astragalus root, scutellaria root, phellodendron bark, cherry bark, coptis rhizome, polygala root, Artemisia leaf, polygonum root, pueraria root, aluminum silicate hydrate with silicon dioxide, trichosanthes root, trichosanthes seed, glycyrrhiza, platycodon root, immature orange, chrysanthemum flower, citrus peel, Notopterygium, apricot kernel, sophora root, schizonepeta spike, cinnamon twig, Koi, safflower, cyperus rhizome, brown rice, magnolia bark, achyranthes root, Euodia fruit, burdock fruit, sesame, schisandra fruit, Bupleurum root, Asiasarum root, green tea leaf, crataegus fruit, gardenia fruit, cornus fruit, Japanese zanthoxylum peel, jujube seed, dioscorea rhizome, rehmannia root, lycium bark, lithospermum root, tribulus fruit, peony root, plantago seed, amomum seed, ginger, wheat seed, cimicifuga rhizome, magnolia flower, malted rice, malted rice, gypsum, cnidium rhizome, Peucedanum root, Nuphar rhizome, cicada slough, mulberry bark, sappan wood, perilla herb, rhubarb, jujube, alisma tuber, bamboo culm, anemarrhena rhizome, clove, uncaria hook, polyporus sclerotium, citrus unshiu peel, arisaema tuber, gastrodia tuber, asparagus root, benincasa seed, Japanese angelica root, peach kernel, eucommia bark, aralia rhizome, ginseng, lonicera leaf and stem, lonicera leaf and stem, fritillaria bulb, malt, ophiopogon root, mentha herb, pinellia tuber, lilium bulb, angelica dahurica root, atractylodes rhizome, loquat leaf, areca, poria sclerotium, processed aconite root, Sinomenium stem and rhizome, sodium sulfate hydrate, Saposhnikovia root and rhizome, Quercus bark, moutan bark, oyster shell, ephedra herb, hemp fruit, akebia stem, saussurea root, leonurus herb, coix seed, longan aril, longgu, Japanese gentian, Alpinia officinarum rhizome, forsythia fruit, Nelumbo seed, and the like.

(57) Vitamins

Vitamin A, vitamin D, vitamin E, vitamin K, vitamin B1, vitamin B2, vitamin B6, vitamin B12, folic acid, niacin, biotin, pantothenic acid, vitamin C, and derivatives thereof, and the like.

(58) Amino Acids

Glycine, alanine, serine, threonine, valine, leucine, asparagine, aspartic acid, isoleucine, proline, glutamine, glutamic acid, phenylalanine, tryptophan, histidine, arginine, tyrosine, methionine, cysteine, lysine, and derivatives thereof, and the like.

(59) Animal Drugs

Aivlosin, spiramycin, aspoxicillin, amoxicillin, oxytetracycline, ampicillin, erythromycin, kitasamycin, cloxacillin, chloramphenicol, dicloxacillin, josamycin, sedecamycin, cefazolin, cefalonium, ceftiofur, cefuroxime, tylosin, tiamulin, tilmicosin, destomycin A, terdecamycin, nystatin, nanafrocin, nafcillin, novobiocin, hygromycin B, bicozamycin, tetracycline, benzylpenicillin, fosfomycin, oleandomycin, mirosamicin, mecillinam, monensin, chlortetracycline, spectinomycin, doxycycline, lincomycin, dexamethasone, apramycin, kanamycin, streptomycin, gentamycin, colistin, fradiomycin, pyromidic acid, or derivatives thereof, and salts thereof, and the like.

(60) Others

Meclofenoxate, tiapride, ifenprodil, nicergoline, fasudil, sumatriptan, dutasteride, oxyfedrine, protokylol, alloclamide, cinepazide maleate, cyclandelate, cinnarizine, pentoxifylline, ifenprodil, rotenone, Amytal, antimycin A, valinomycin, gramicidin A, oligomycin, edaravone, citicoline, methylphenidate, modafinil, mazindol, picrotoxin, pentetrazole, strychnine, carperitide, dilazep, doxapram, pirenoxine, glutathione, naphazoline, hyaluronic acid, acetaminophen, teceleukin, celmoleukin, cilastatin, betamipron, pyrimethamine, gimeracil, oteracil, uracil, hydroxy-CAM, diacerein, megestrol acetate, nicergoline, diethyl benzylphosphonate, and the like, and further, phenolsulfonphthalein derivatives, benzothiopyran or benzothiepine derivatives, thienoindazole derivatives, fumagillol derivatives, a P38 MAP kinase inhibitor (e.g., a thiazole-based compound described in WO 00/64894 or the like), a matrix metalloprotease inhibitor (MMPI), an ischemic disease therapeutic agent, an immunological disease therapeutic agent, an angiogenesis therapeutic agent, a retinopathy therapeutic agent, a retinal vein occlusion therapeutic agent, a senile disciform macular degeneration therapeutic agent, a cerebral vasospasm therapeutic agent, a cerebral thrombosis therapeutic agent, a cerebral infarction therapeutic agent, a cerebral occlusion therapeutic agent, a cerebral hemorrhage therapeutic agent, a subarachnoid hemorrhage therapeutic agent, a hypertensive encephalopathy therapeutic agent, a transient cerebral ischemic attack therapeutic agent, a multiinfarct dementia therapeutic agent, an arteriosclerosis therapeutic agent, a Huntington's disease therapeutic agent, a brain tissue disorder therapeutic agent, an optic neuropathy therapeutic agent, an ocular hypertension therapeutic agent, a retinal detachment therapeutic agent, an arthritis therapeutic agent, an anti-sepsis drug, an anti-septic shock drug, an atopic dermatitis therapeutic agent, an allergic rhinitis therapeutic agent, a congenital heart disease therapeutic agent, a lymphadenitis therapeutic agent, a Crohn's disease therapeutic agent, a ulcerative colitis therapeutic agent, an irritable bowel syndrome therapeutic agent, a renal failure therapeutic agent, an oxytocic, an infertility therapeutic agent, an ecbolic, a tocolytic, a forced abortion drug, a benign prostatic hyperplasia therapeutic agent, an endometrial cancer therapeutic agent, a breast cancer therapeutic agent, a chronic obstructive pulmonary disease therapeutic agent, a brain tumor therapeutic agent, a migraine therapeutic agent, a hepatitis therapeutic agent, an ascites therapeutic agent, an edema therapeutic agent, a Meniere's disease therapeutic agent, a dyschromia therapeutic agent, a Hansen's disease therapeutic agent, a pesticide antidote, a decubitus ulcer therapeutic agent, an osteoarthritis therapeutic agent, an osteomalacia (rickets) therapeutic agent, a dermatophytosis therapeutic agent, and the like.

Poorly soluble drugs, such as griseofulvin, hydrochlorothiazide, probucol, tolbutamide, fenofibrate, flurbiprofen, naproxen, piroxicam, albendazole, phenytoin, dipyridamole, acyclovir, indomethacin, and furosemide.

The following components are preferred as the pesticide compounds that are poorly water-soluble components.

(1) Insecticides (A) Carbamate-based: MIPC: isoprocarb, BPMC: fenobucarb, MPMC: xylylcarb, XMC, NAC: carbaryl, bendiocarb, carbofuran, and the like.

(B) Synthetic pyrethroid-based: cypermethrin, fenpropathrin, etofenprox, resmethrin, and the like.

(c) Organophosphorus-based: EPN, cyanofenphos, PAP: phenthoate, CVMP: tetrachlorvinphos, monocrotophos, phosalone, chlorpyrifos-methyl, chlorpyrifos, pyridaphenthion, quinaiphos, DMTP: methidathion, salithion (eioxabenzofos), and the like.

(D) Organochlorine-based: benzoepin (endosulfan) and the like.

(E) Others: bensultap, buprofezin, flufenoxuron, diflubenzuron, chlorfluazuron, imidacloprid, and the like.

(2) Germicides (A) N-heterocyclic ergosterol inhibitors: triflumizole, triforine, and the like.

(B) Carboxamide-based: mepronil, flutolanil, pencycuron, oxycarboxin, and the like.

(c) Dicarboximide-based: iprofione, vinclozolin, procymidone, and the like.

(D) Benzimidazole-based: benomyl and the like.

(E) Polyhaloalkylthio-based: captan and the like.

(F) Organochlorine-based: fthalide, TPN: chlorothalonil, and the like.

(G) Sulfur-based: zineb, maneb, and the like.

(H) Others: diclomezin, tricyclazole, isoprothioldne, probenazole, anilazine, oxolinic acid, ferimzone, and the like.

(3) Herbicides (A) Sulfonylurea-based: imazosulfuron, bensulfuronmEthyl, and the like.

(B) Triazine-based: simetryn, dimethametryn, and the like.

(C) Urea-based: dymron and the like.

(D) Acid amide-based: propanil, mefenacet, and the like.

(E) Carbamate-based: swep and the like.

(F) Diazol-based: oxadiazon, pyrazolate, and the like.

(G) Dinitroaniline-based: trifluralin and the like.

(H) Others: dithiopyr and the like.

The content of the medicinal component in the tablet is preferably from about 0.1 mass % to about 90 mass %, more preferably from about 1 mass % to about 80 mass %. When the content of the medicinal component falls within the above-mentioned range, hygroscopicity, stability of a formulation, binding property, disintegrability, and the like are improved.

(3) Functional Particles

The functional particles are preferably at least one kind of component selected from the group consisting of bitterness-masking particles and sustained-release particles.

The bitterness-masking particles are preferably polymer-coated particles, drug matrix particles having imparted thereto a bitterness-masking function, bitterness-masked drug granulated particles, or the like.

The sustained-release particles are preferably polymer-coated sustained-release particles, enteric polymer-coated particles, or the like.

It is preferred that at least one kind of component selected from those components be used.

The content of the functional particles in the tablet is preferably from about 0.1 mass % to about 90 mass %, more preferably from about 1 mass % to about 80 mass %. When the content of the functional particles falls within the above-mentioned range, hygroscopicity, stability of a formulation, binding property, disintegrability, and the like are improved.

(4) Additive

The composite granulated product and tablet of the present invention may include other additives in addition to the above-mentioned components.

Plasticizers, for example: polyhydric alcohols, such as glycerin, ethylene glycol, and propylene glycol; various waxes, such as monostearin, PEG 4000, PEG 6000, and PEG 20000; organic fatty acids, such as stearic acid and magnesium stearate; surfactants, such as triethyl citrate, Tween 80, HCO-60, and triacetin; and viscosity modifiers, such as simple syrup, a glucose solution, a starch solution, and a gelatin solution.

Absorption promoters, such as a quaternary ammonium salt and sodium lauryl sulfate.

Adsorbents, such as starch, lactose, kaolin, bentonite, and colloidal silicic acid.

Lubricants, such as magnesium stearate, calcium stearate, talc, magnesium oxide, colloidal silica, boric acid powder, and polyethylene glycol.

Dispersants, such as sucrose fatty acid ester, sorbitan fatty acid ester, and saponin.

Antioxidants, such as ascorbic acid and tocopherol.

Acidulants, such as lactic acid, citric acid, gluconic acid, and glutamic acid.

Sweeteners, such as sucralose, acesulfame potassium, aspartame, and glycyrrhizin.

Flavors, such as mint oil, eucalyptus oil, cinnamon oil, fennel oil, clove oil, orange oil, lemon oil, rose oil, fruit flavor, mint flavor, peppermint powder, d,l-menthol, and 1-menthol.

A stabilizer, a surfactant, a modifier, a lubricant, a capsule coating, a solubilizer, a reducing agent, a buffer, a sweetener, a base, a volatilizing aid, a taste masking agent, a synergist, a suspending agent, an antioxidant, a glossing agent, an efficacy enhancer, a coating agent, a coating, a support, a sustaining agent, a wetting agent, a moisture-controlling agent, a filler, a defoaming agent, a cooling agent, a feeding stimulant, an adhesive, an enhancer, a masticatory, a flavoring agent, a coloring agent, a sugar coating agent, a tonicity agent, a softener, an emulsifier, a combustion agent, a pressure-sensitive adhesive, a pressure-sensitive adhesion enhancer, a viscous agent, a thickening agent, an inflammation suppressant, an exothermic agent, a foaming agent, a pH adjuster, a skin protectant, a flotation agent, a dispersant, a propellant, a disintegrating agent, a disintegration aid, an aromatic, a corrosion inhibitor, a preservative, an analgesic, an attractant, a solubilizing agent, a dissolution aid, a solvent, a release agent, a fluidizer, and the like.

(5) Orally Disintegrating Tablet (OD Tablet)

The tablet of the present invention is preferably an OD tablet.

When an OD tablet is produced using the composite granulated product of the present invention, the following OD tablet can be obtained:

the OD tablet has proper hardness and is also excellent in disintegrability, and the OD tablet maintains its proper hardness and disintegrability even under high temperature and increased humidity, and hence is excellent in storage stability.

In a balance between disintegrability and hardness, when the disintegrability is rapid (rapid disintegrability), the hardness generally tends to lower. This relationship is manifested in a relationship among the tableting pressure, hardness, and disintegration time of a tablet. The tablet of the present invention maintains disintegrability and hardness in good balance as an OD tablet.

For example, in a comparison between Comparative Example 1 and Example 4 to be described below, when the disintegration time is shortened, the hardness tends to be slightly low. The addition of 15% of PH101 in additional Examples can achieve both rapid disintegration and proper hardness (high hardness).

In pharmaceutical approval and licensing, the disintegration time and hardness of a rapidly disintegrating tablet are not standardized in Japan.

An 8φ and 200 mg tablet is a rapidly disintegrating tablet when its disintegration time is about 30 seconds or less.

A hardness of 50 N or more is a general hardness.

According to an orally disintegrating tablet handbook, a 7 mm to 8 mm tablet needs to have a tablet hardness of from 3 kgf to 5 kgf or more (29.4 N to 49 N).

That is, in the case of 8φ, a hardness of 40 N or more is an appropriate hardness, and is a recent design target (Yoshinori Masuda: Orally Disintegrating Tablet Handbook—On Additives—PHARM TECH JAPAN 31(4) 10-15 (2015) Chapter 3).

[3] Manufacturing Method for Composite Granulated Product

The present invention is directed to a composite granulated product including a sugar or a sugar alcohol, a swelling binder, a disintegrating agent, and a highly absorbent excipient.

The composite granulated product includes a sugar or a sugar alcohol, a swelling binder, a disintegrating agent (first disintegrating agent), and a highly absorbent excipient, and is manufactured by a manufacturing method including the steps of:

(1) performing wet granulation by mixing the sugar or the sugar alcohol, the swelling binder, and the first disintegrating agent using a binding solution;

(2) performing layering on the granulated product of the step (1) with addition of a highly absorbent excipient to the granulated product obtained in the step (1); and (3) performing layering on the granulated product obtained in the step (2) with addition of a second disintegrating agent to the granulated product obtained in the step (2).

The composite granulated product includes a sugar or a sugar alcohol, a swelling binder, a disintegrating agent, and a highly absorbent excipient, and is manufactured by a manufacturing method including the steps of:

(1) performing wet granulation by mixing a sugar or a sugar alcohol, a swelling binder, and a first disintegrating agent using a binding solution;

(2) performing granulation with addition of a highly absorbent excipient to a granulated product obtained in the step (1); and (3) performing granulation with addition of a second disintegrating agent to a granulated product obtained in the step (2), the first disintegrating agent and the second disintegrating agent each being at least one kind of component selected from the group consisting of hydroxypropyl cellulose, crospovidone, starch, croscarmellose sodium, carmellose calcium, carmellose, partially pregelatinized starch, carboxymethyl starch sodium, and sodium starch glycolate.

Preferred Conditions of Step (1)

The granulation composition (ratio to total mass) of the sugar or the sugar alcohol (D-mannitol or the like) is preferably from about 70 mass % to about 95 mass %, more preferably from about 80 mass % to about 90 mass %.

The granulation composition (ratio to total mass) of the swelling binder (PVA-based polymer or the like) is preferably from about 0.05 mass % to about 3 mass %, more preferably from about 0.5 mass % to about 2 mass %.

The granulation composition (ratio to total mass) of the first disintegrating agent (L-HPC or the like) is preferably from about 5 mass % to about 20 mass %, more preferably from about 8 mass % to about 15 mass %.

The amount of the binding solution is preferably from about 10 mass % to about 25 mass %, more preferably from about 12 mass % to about 22 mass %.

With regard to the conditions of the wet granulation, agitation granulation is preferably used because of a simple manufacturing process.

The period of time for which the wet granulation is performed is preferably from about 2 minutes to about 10 minutes.

In the manufacturing method for a composite granulated product, as the sugar or the sugar alcohol, at least one kind of component selected from the group consisting of D-mannitol, trehalose, xylitol, erythritol, lactose, and sucrose is preferably used.

In the manufacturing method for a composite granulated product, as the swelling binder, at least one kind of component selected from the group consisting of a polyvinyl alcohol-based polymer, partially pregelatinized starch, hydroxypropyl cellulose, and crystalline cellulose is preferably used.

In the manufacturing method for a composite granulated product, the average particle diameter of the swelling binder is preferably from 10 μm to 200 μm.

Steps (2) and (3)

The steps (2) and (3) involve performing granulation with addition of the highly absorbent excipient to the granulated product obtained in the above-mentioned step (step (2)), and then performing granulation with addition of a second disintegrating agent to the obtained granulated product (step (3)), and are layering granulation steps for the granulated product.

These steps constitute the compositing of the composite granulated product.

In the manufacturing method for a composite granulated product, at least one kind of component selected from the group consisting of light anhydrous silicic acid, hydrated silicon dioxide, calcium silicate, magnesium aluminometasilicate, starch, calcium carbonate, kaolin, silicic acid, potassium hydrogen phosphate, calcium hydrogen phosphate, sodium hydrogen phosphate, dipotassium phosphate, disodium phosphate, potassium dihydrogen phosphate, calcium dihydrogen phosphate, sodium dihydrogen phosphate, calcium lactate, magnesium aluminosilicate, calcium silicate, and magnesium silicate is preferably used as the highly absorbent excipient.

Preferred Conditions of Step (2)

The step (2) is a step of subjecting the composite granulated product to layering granulation.

The granulation composition (ratio to total mass) of the highly absorbent excipient (light anhydrous silicic acid, hydrated silicon dioxide, or the like) is preferably from about 0.5 mass % to about 5 mass %, more preferably from about 1 mass % to about 3 mass %.

With regard to the conditions of the layering granulation, the highly absorbent excipient is preferably added as powder, and an agitation granulator is preferably used to facilitate the powder addition.

A granulation time is preferably from about 2 minutes to about 20 minutes. The following effect is obtained: the progress of the granulation (increase in particle diameter) is suppressed, the size of the granulated product is maintained at about 200 μm or less, and the granulated product does not increase in size.

Preferred Conditions of Step (3)

The step (3) is a step of layering granulation.

The granulation composition (ratio to total mass) of the second disintegrating agent (starch (corn starch or the like), crospovidone, croscarmellose sodium, or the like) is preferably from about 2 mass % to about 15 mass %, more preferably from about 2 mass % to about 10 mass %.

With regard to the conditions of the layering granulation, the second disintegrating agent is preferably added as powder, and an agitation granulator is preferably used to facilitate the powder addition.

The period of time for which the wet granulation is performed is preferably from 2 minutes to 20 minutes.

When the second disintegrating agent is allowed to adhere to the surface of the granulated product, the following effect is obtained with a small addition amount thereof when the granulated product is tableted: the capacity for water absorption into the inside of the tablet is enhanced (water-conducting effect).

In the manufacturing method for a composite granulated product, hydroxypropyl cellulose is preferably used as the first disintegrating agent, and at least one kind of component selected from the group consisting of starch, crospovidone, and croscarmellose sodium is preferably used as the second disintegrating agent.

A composite granulated product may be manufactured by the manufacturing method for a composite granulated product.

In the manufacturing method for a composite granulated product, the composite granulated product is preferably a composite granulated product for an orally disintegrating tablet.

When an OD tablet is produced using the obtained composite granulated product, the following OD tablet can be obtained:

the OD tablet has appropriate hardness and is also excellent in disintegrability, and the OD tablet maintains its high hardness and disintegrability even under high temperature and increased humidity, and hence is excellent in storage stability.

First Disintegrating Agent and Second Disintegrating Agent

When an OD tablet is produced using the composite granulated product manufactured by the manufacturing method for a composite granulated product of the present invention, the OD tablet has high hardness and is also excellent in disintegrability.

The OD tablet maintains its high hardness and disintegrability even under high temperature and increased humidity, and hence is excellent in storage stability.

As described above, the manufacturing method can produce a composite granulated product optimal for producing an excellent OD tablet.

The manufacturing method has a feature of including the step (1) of performing wet granulation by mixing the sugar or the sugar alcohol, the swelling binder, and the first disintegrating agent, the subsequent step (2) of performing granulation with addition of the highly absorbent excipient to the granulated product obtained in the step (1), and the subsequent step (3) of performing granulation with addition of the second disintegrating agent to the granulated product obtained in the step (2).

The manufacturing method includes the first step (1) of performing wet granulation using the first disintegrating agent, and includes, as the subsequent steps (2) and (3), layering granulation steps for the granulated product, of performing granulation with addition of the highly absorbent excipient to the obtained granulated product, and further performing granulation with addition of the second disintegrating agent to the obtained granulated product.

Those steps constitute the compositing of the composite granulated product.

The steps (2) and (3) are referred to as layering granulation.

In the manufacturing method, a granulated product including the first disintegrating agent is formed, and is granulated with the highly absorbent excipient, and a granulated product in which the resultant is further composited with the second disintegrating agent is produced.

Through such layering granulation (surface-modifying granulation), the surface of the granulated product is modified.

In addition, in the manufacturing method, the second disintegrating agent is allowed to adhere to the surface of the granulated product including the first disintegrating agent (step (1)) and obtained by being granulated with the addition of the highly absorbent excipient (step (2)), and hence, with a smaller addition amount thereof, there can be produced a composite granulated product having the following effect when tableted: the capacity for water absorption into the inside of the tablet is enhanced (water-conducting effect).

That is, an OD tablet produced using the composite granulated product is excellent in hardness, disintegrability, and storage stability.

The effect achieved by the layering granulation steps included in the manufacturing method for a composite granulated product has been demonstrated through a dissolution test and a stability test in Examples to be described later.

In the manufacturing method for a composite granulated product of the present invention, it is important that the composite granulated product having a modified surface be produced by forming layers on the granulated product through the step (1) of performing granulation with addition of the first disintegrating agent, then the step (2) of performing granulation with addition of the highly absorbent excipient, and then the step (3) of performing granulation with addition of the second disintegrating agent (layering granulation).

It is important that the manufacturing method involve the layering granulation steps of adding the first disintegrating agent and the second disintegrating agent in two separate stages.

In the manufacturing method for a composite granulated product, the invention is clear even when a difference between the first disintegrating agent and the second disintegrating agent is not specified.

A preferred mode of the manufacturing method for a composite granulated product is as follows:

hydroxypropyl cellulose is used as the first disintegrating agent, and starch, crospovidone, croscarmellose sodium, or the like is used as the second disintegrating agent.

The disintegrating agents to be used in the manufacturing method for a composite granulated product are specified.

The use of the first disintegrating agent and the second disintegrating agent in the manufacturing method for a composite granulated product is utilized and effective also in a manufacturing method for a granule for tableting or a manufacturing method for a tablet.

Step of Preparing Granule for Tableting

A granule for tableting may be manufactured by including (4) a step of adding and mixing at least one kind of hardness modifier selected from the group consisting of crystalline cellulose, a D-mannitol granulated product, and isomalt into a composite granulated product obtained by the above-mentioned manufacturing method for a composite granulated product.

A granule for tableting may be manufactured by adding and mixing a hardness modifier into the composite granulated product.

It is preferred that the granule for tableting be manufactured by a manufacturing method including (4) a step of adding and mixing at least one kind of hardness modifier selected from the group consisting of crystalline cellulose (microcrystalline cellulose), a D-mannitol granulated product, and isomalt into the composite granulated product obtained in the step (3).

The granule for tableting is one mode of the composite granulated product.

Preferred Conditions of Step of Preparing Granule for Tableting (Step (4))

The amount of the hardness modifier (microcrystalline cellulose or the like) is preferably from about 5 mass % to about 30 mass %, more preferably from about 10 mass % to about 20 mass %.

A period of time may be adjusted in accordance with an implementation scale and a mixer, and is generally preferably from about 5 minutes to about 20 minutes.

The following effect is obtained: the tablet hardness at the same tableting pressure is increased.

The obtained composite granulated product is a wet mass, and is preferably dried.

It is preferred that: an additive and functional particles be added to the composite granulated product or the granule for tableting; then about 0.5% of a lubricant (magnesium stearate or the like) be added and mixed into the mixture; and then tableting be performed with a tableting machine.

When an OD tablet is produced using the obtained composite granulated product, the following OD tablet can be obtained:

the OD tablet has appropriate hardness and is also excellent in disintegrability, and the OD tablet maintains its high hardness and disintegrability even under high temperature and increased humidity, and hence is excellent in storage stability.

As a binding solution, water, an aqueous solution of a PVA copolymer, an aqueous solution of PVA, an aqueous solution of hydroxypropyl cellulose, an aqueous solution of polyvinylpyrrolidone, or the like may be used. Of those, water is preferred.

Those binding solutions may be used in combination thereof. As the binding solution, an aqueous solution having low concentration, such as 3 mass % of a PVA-based copolymer, may be used.

In the manufacturing method for a granule for tableting, the granule for tableting is preferably a granule for tableting for an orally disintegrating tablet.

Manufacturing Method for Tablet

A tablet may be manufactured by mixing a medicinal component and functional particles, and a composite granulated product obtained by the above-mentioned manufacturing method for a composite granulated product, or the above-mentioned granule for tableting.

The tablet is preferably manufactured by a method including the steps of:

adding and mixing drug functional particles and a lubricant (magnesium stearate or the like, about 0.5%) into the composite granulated product; and then performing tableting.

In the manufacturing method for a tablet, as the functional particles, at least one kind of component selected from the group consisting of bitterness-masking particles and sustained-release particles is preferably used.

The manufacturing method for a tablet preferably further includes adding and mixing a lubricant.

In the manufacturing method for a tablet, the tablet is preferably an orally disintegrating tablet.

In the tableting step, the compositional ratio of the composite granulated product in the tablet is preferably from about 29 wt % to about 97 wt %.

The ratio of the functional particles in the tablet is preferably from about 2 wt % to about 70 wt %.

The ratio of the lubricant in the tablet is preferably from about 0.1 wt % to about 1 wt %.

The tablet is preferably manufactured by a method including the steps of:

adding, to the composite granulated product, drug functional particles, and at least one kind of hardness modifier selected from the group consisting of crystalline cellulose, a D-mannitol granulated product, and isomalt; then adding and mixing a lubricant (magnesium stearate or the like, about 0.5%);

and then performing tableting.

In the tableting step, the compositional ratio of the composite granulated product in the tablet is preferably from about 5 wt % to about 95 wt %.

The ratio of the functional particles in the tablet is preferably from about 2 wt % to about 70 wt %.

The ratio of the hardness modifier in the tablet is preferably from about 2 wt % to about 25 wt %.

The ratio of the lubricant in the tablet is preferably from about 0.1 wt % to about 1 wt %.

The tablet is preferably manufactured by a manufacturing method including the steps of:

adding and mixing a medicinal component and functional particles, and at least one kind of hardness modifier selected from the group consisting of crystalline cellulose, D-mannitol, and isomalt into the composite granulated product; and then performing tableting.

When an OD tablet is produced using the obtained composite granulated product, the following OD tablet can be obtained:

the OD tablet has high hardness and is also excellent in disintegrability, and the OD tablet maintains its high hardness and disintegrability even under high temperature and increased humidity, and hence is excellent in storage stability.

The composite granulated product manufactured by the above-mentioned manufacturing method for a composite granulated product, and the granule for tableting manufactured by the above-mentioned manufacturing method for a granule for tableting are prepared through the layering granulation steps of adding the first disintegrating agent and the second disintegrating agent in two stages.

The OD tablet produced using such composite granulated product or granule for tableting is excellent in hardness, disintegrability, and storage stability.

This effect is due to the granulated product having a modified surface, which is provided by the layering granulation steps included in the manufacturing method therefor, and can be identified on the basis of the process (production process) for obtaining the surface-modified granulation product.

As a product of a manufacturing method, the composite granulated product or the granule for tableting is different from the related art in consideration of its materials and manufacturing process, and the difference can be distinguished on the basis of the manufacturing process.

EXAMPLES

Now, the present invention is described in more detail by way of Examples. However, the present invention is not limited to these Examples.

In the following Examples and Comparative Examples, investigations were performed using materials and test methods described below.

(1) Example 1 Aero/Cons Layering Granulation

Raw Material

HMM: mannitol obtained by pulverizing D-mannitol (MM, Marine Crystal: Mitsubishi Shoji Foodtech Co., Ltd.) (speed mill: Fuji Paudal Co., Ltd., 1 mm herringbone)

Pea-25: PEARLITOL 25C (D-mannitol: Rocket)

Crystalline cellulose (CEOLUS PH101: Asahi Kasei Corporation)

Low-substituted hydroxypropyl cellulose (L-HPC, LH-21: Shin-Etsu Chemical Co., Ltd.)

PVA-based polymer: POVACOAT Type MP (Daido Chemical Industry Co., Ltd.)

Formulation and Loading Amount

| Initial granulation: | HMM/Pea-25 = 1/1 | 85% | 34 g |
|---|---|---|---|
| | CEOLUS PH101 | 3.5% | 1.4 g |
| | L-HPC LH21 | 10.5% | 4.2 g |
| | POVACOAT Type MP | 1% | 0.4 g |

Layering granulation step 1: Aerosil 200 (hydrophilic fumed silica: Evonik Industries AG), 0.72 g (1.8% in outer percentage)

Layering granulation step 2: corn starch (corn starch: Nippon Starch Chemical Co., Ltd.), 2 g (5.0% in outer percentage)

Granulation Method

Horizontal twin-blade agitation granulator (mixer torque rheometer: Caleva)

Initial granulation step: blade rotation speed: 125 rpm, 3 minutes, amount of granulation liquid: 11.1 g of purified water Layering granulation step 1: blade rotation speed: 50 rpm, 12 minutes Layering granulation step 2: blade rotation speed: 50 rpm, 5 minutes The compositing of a composite granulated product was treatment involving the following steps:

(1) performing wet granulation by mixing D-mannitol (sugar or sugar alcohol), a PVA-based polymer (swelling binder), crystalline cellulose (swelling binder), and L-HPC (first disintegrating agent) using a binding solution;

(2) performing granulation with addition of hydrophilic fumed silica (highly absorbent excipient) to the granulated product obtained in the step (1) (layering granulation step); and (3) performing granulation with addition of corn starch (second disintegrating agent) to the granulated product obtained in the step (2) (layering granulation step).

Drying Method

Shelf-type forced-air drying: 60° C., 3 hours

Powder Characteristics of Obtained Dry Granulated Product

Average particle diameter: 98.6 μm

Compressibility: 32.7%

Tapped specific volume: 1.85 mL/g

Hydraulic Press

Granules loaded into a die (11.3 φ) were formed with S-04-127 manufactured by Riken Kiki Co., Ltd. (pressure receiving area: 6.42 cm$^2$). For example, a pressure of 300 kg/cm$^2$ corresponds to 18.87 kN on the basis of 300×9.8× 6.42.

This corresponds to about 11.8 kN in the case of an tablet, which serves as a standard in a formability evaluation method.

The resultant formed plate was evaluated for its hardness (hardness meter manufactured by Okada Seiko Co., Ltd.) and disintegration time (the Japanese Pharmacopoeia) with a disintegration tester manufactured by Toyama Sangyo Co., Ltd. and purified water at 37° C.

30% each of a placebo (containing no model particles), vitamin C-granulated product (VC97: BASF), and EUDRAGIT-coated bitterness-masking model particles (functional particles, RSPO-FC: manufactured by Pharma Polytech Inc.) were mixed, and an 11 φ and 300 mg flat tablet was prepared with a hydraulic press (manufactured by Rigaku) and was evaluated.

Evaluation Results of Formability and Disintegrability of Example 1 (Table 1)

TABLE 1

| Forming | Placebo | | VC97 30% | | RSPO-FC 30% | |
|---|---|---|---|---|---|---|
| pressure (Kg/cm$^2$) | Hardness (N) | Disintegration (sec) | Hardness (N) | Disintegration (sec) | Hardness (N) | Disintegration (sec) |
| 300 | 126.2 | 16 | 106.8 | 63 | 57.9 | 11 |
| 250 | 117.8 | 15 | 96.3 | 52 | 56.5 | 9 |
| 200 | 104.9 | 14 | 73.6 | 32 | 46.6 | 8 |
| 150 | 74.9 | 12 | 60.9 | 24 | 34.2 | 6 |
| 100 | 53.5 | 11 | 42.4 | 16 | 24.3 | 5 |

(2) Example 2 Aero/Kollidon CL Layering Granulation Raw Material

HMM: mannitol obtained by pulverizing D-mannitol (MM, Marine Crystal: Mitsubishi Shoji Foodtech Co., Ltd.) (speed mill: Fuji Paudal Co., Ltd., 1 mm herringbone)

Pea-25: PEARLITOL 25C (D-mannitol: Rocket)

Crystalline cellulose (CEOLUS PH101: Asahi Kasei Corporation)

Low-substituted hydroxypropyl cellulose (L-HPC, LH-21: Shin-Etsu Chemical Co., Ltd.)

PVA-based polymer: POVACOAT Type MP (Daido Chemical Industry Co., Ltd.)

Formulation and Loading Amount

| Initial granulation: | HMM/Pea-25 = 1/1 | 85% | 34 g |
|---|---|---|---|
| | CEOLUS PH101 | 3.5% | 1.4 g |
| | L-HPC LH21 | 10.5% | 4.2 g |
| | POVACOAT Type MP | 1% | 0.4 g |

Layering granulation step 1: Aerosil 200 (hydrophilic fumed silica: Evonik Industries AG), 0.72 g (1.8% in outer percentage)

Layering granulation step 2: Kollidon (crospovidone: Kollidon CL, BASF), 2 g (5.0% in outer percentage)

Granulation Method

Horizontal twin-blade agitation granulator (mixer torque rheometer: Caleva)

Initial granulation step: blade rotation speed: 125 rpm, 3 minutes, amount of granulation liquid: 11.1 g of purified water Layering granulation step 1: blade rotation speed: 50 rpm, 12 minutes Layering granulation step 2: blade rotation speed: 50 rpm, 5 minutes The compositing of a composite granulated product was treatment involving the following steps:

(1) performing wet granulation by mixing D-mannitol (sugar or sugar alcohol), a PVA-based polymer (swelling binder), crystalline cellulose (swelling binder), and L-HPC (first disintegrating agent) using a binding solution;

(2) performing granulation with addition of hydrophilic fumed silica (highly absorbent excipient) to the granulated product obtained in the step (1) (layering granulation step); and (3) performing granulation with addition of crospovidone (second disintegrating agent) to the granulated product obtained in the step (2) (layering granulation step).

Drying Method

Shelf-type forced-air drying: 60° C., 3 hours

Powder Characteristics of Obtained Dry Granulated Product Average particle diameter: 111.2 μm Compressibility: 28.8%

Tapped specific volume: 1.78 mL/g

Hydraulic Press

Granules loaded into a die (11.3 φ) were formed with S-04-127 manufactured by Riken Kiki Co., Ltd. (pressure receiving area: 6.42 cm$^2$). For example, a pressure of 300 kg/cm$^2$ corresponds to 18.87 kN on the basis of 300×9.8× 6.42.

This corresponds to about 11.8 kN in the case of an tablet, which serves as a standard in a formability evaluation method.

The resultant formed plate was evaluated for its hardness (hardness meter manufactured by Okada Seiko Co., Ltd.) and disintegration time (the Japanese Pharmacopoeia) with a disintegration tester manufactured by Toyama Sangyo Co., Ltd. and purified water at 37° C.

30% each of a placebo (containing no model particles), vitamin C-granulated product (VC 97: BASF), and EUDRAGIT-coated bitterness-masking model particles (functional particles, RSPO-FC: manufactured by Pharma Polytech Inc.) were mixed, and an 11 φ and 300 mg flat tablet was prepared with a hydraulic press (manufactured by Rigaku) and was evaluated.

Evaluation Results of Formability and Disintegrability of Example 2 (Aero/Kollidon) (Table 2)

TABLE 2

| Forming | Placebo | | VC97 30% | | RSPO-FC 30% | |
|---|---|---|---|---|---|---|
| pressure (Kg/cm$^2$) | Hardness (N) | Disintegration (sec) | Hardness (N) | Disintegration (sec) | Hardness (N) | Disintegration (sec) |
| 300 | 127.9 | 12 | 100.7 | 39 | 64.7 | 9 |
| 250 | 105.3 | 13 | 90.8 | 29 | 56.9 | 7 |
| 200 | 93.3 | 10 | 78.3 | 18 | 50.3 | 6 |
| 150 | 64.9 | 10 | 55.9 | 15 | 38.2 | 5 |
| 100 | 46.8 | 10 | 32.4 | 11 | 21.9 | 6 |

(3) Example 3 Aero/Ac-Di-Sol Layering Granulation Raw Material

HMM: mannitol obtained by pulverizing D-mannitol (MM, Marine Crystal: Mitsubishi Shoji Foodtech Co., Ltd.) (speed mill: Fuji Paudal Co., Ltd., 1 mm herringbone)

Pea-25: PEARLITOL 25C (D-mannitol: Rocket)

Crystalline cellulose (CEOLUS PH101: Asahi Kasei Corporation)

Low-substituted hydroxypropyl cellulose (L-HPC, LH-21: Shin-Etsu Chemical Co., Ltd.)

PVA-based polymer: POVACOAT Type MP (Daido Chemical Industry Co., Ltd.)

Formulation and Loading Amount

| Initial granulation: | HMM/Pea-25 = 1/1 | 85% | 34 g |
|---|---|---|---|
| | CEOLUS PH101 | 3.5% | 1.4 g |
| | L-HPC LH21 | 10.5% | 4.2 g |
| | POVACOAT Type MP | 1% | 0.4 g |

Layering granulation step 1: Aerosil 200 (hydrophilic fumed silica: Evonik Industries AG), 0.72 g (1.8% in outer percentage)

Layering granulation step 2: Ac-Di-Sol (croscarmellose sodium: FMCF), 2 g (5.0% in outer percentage)

Granulation Method

Horizontal twin-blade agitation granulator (mixer torque rheometer: Caleva)

Initial granulation step: blade rotation speed: 125 rpm, 3 minutes, amount of granulation liquid: 11.1 g of purified water Layering granulation step 1: blade rotation speed: 50 rpm, 12 minutes Layering granulation step 2: blade rotation speed: 50 rpm, 5 minutes The compositing of a composite granulated product was treatment involving the following steps:

(1) performing wet granulation by mixing D-mannitol (sugar or sugar alcohol), a PVA-based polymer (swelling binder), crystalline cellulose (swelling binder), and L-HPC (first disintegrating agent) using a binding solution;

(2) performing granulation with addition of hydrophilic fumed silica (highly absorbent excipient) to the granulated product obtained in the step (1) (layering granulation step); and (3) performing granulation with addition of croscarmellose sodium (second disintegrating agent) to the granulated product obtained in the step (2) (layering granulation step).

Drying Method

Shelf-type forced-air drying: 60° C., 3 hours

Powder Characteristics of Obtained Dry Granulated Product

Average particle diameter: 88.0 μm

Compressibility: 28.6%

Tapped specific volume: 1.75 mL/g

Hydraulic Press

Granules loaded into a die (11.3 φ) were formed with S-04-127 manufactured by Riken Kiki Co., Ltd. (pressure receiving area: 6.42 cm$^2$). For example, a pressure of 300 kg/cm$^2$ corresponds to 18.87 kN on the basis of 300×9.8×6.42.

This corresponds to about 11.8 kN in the case of an tablet, which serves as a standard in a formability evaluation method.

The resultant formed plate was evaluated for its hardness (hardness meter manufactured by Okada Seiko Co., Ltd.) and disintegration time (the Japanese Pharmacopoeia) with a disintegration tester manufactured by Toyama Sangyo Co., Ltd. and purified water at 37° C.

30% each of a placebo (containing no model particles), vitamin C-granulated product (VC 97: BASF), and EUDRAGIT-coated bitterness-masking model particles (functional particles, RSPO-FC: manufactured by Pharma Polytech Inc.) were mixed, and an 11 φ and 300 mg flat tablet was prepared with a hydraulic press (manufactured by Rigaku) and was evaluated.

Evaluation Results of Formability and Disintegrability of Example 3 (Aero/Ac-Di-Sol) (Table 3)

(4) Example 4 Aero/XL-10 Layering Granulation

Raw Material

HMM: mannitol obtained by pulverizing D-mannitol (MM, Marine Crystal: Mitsubishi Shoji Foodtech Co., Ltd.) (speed mill: Fuji Paudal Co., Ltd., 1 mm herringbone)

Pea-25: PEARLITOL 25C (D-mannitol: Rocket) Crystalline cellulose (CEOLUS PH101: Asahi Kasei Corporation)

Low-substituted hydroxypropyl cellulose (L-HPC, LH-21: Shin-Etsu Chemical Co., Ltd.)

PVA-based polymer (POVACOAT Type MP: Daido Chemical Industry Co., Ltd.)

Formulation and Loading Amount

| Initial granulation: | HMM/Pea-25 = 1/1 | 85% | 255 g |
|---|---|---|---|
| | CEOLUS PH101 | 3.5% | 10.5 g |
| | L-HPC LH21 | 10.5% | 31.5 g |
| | POVACOAT Type MP | 1% | 3 g |

Layering granulation step 1: Aerosil 200 (hydrophilic fumed silica: Evonik Industries AG), 5.4 g (1.8% in outer percentage)

Layering granulation step 2: Polyplasdone (crospovidone, XL-10, ISP), 15 g (5.0% in outer percentage)

Granulation Method

High-speed agitation granulator (Vertical Granulator FM-VG-01: Powrex Corporation)

Initial granulation step: blade rotation speed: 250 rpm, chopper rotation speed 1,500 rpm, amount of granulation liquid: 83.5 g of purified water, granulation time: 3 minutes Layering granulation step 1: blade rotation speed: 250 rpm, chopper rotation speed: 1,500 rpm, 2 minutes Layering granulation step 2: blade rotation speed: 250 rpm, chopper rotation: 1,500 rpm, 2 minutes The compositing of a composite granulated product was treatment involving the following steps:

(1) performing wet granulation by mixing D-mannitol (sugar or sugar alcohol), a PVA-based polymer (swelling binder), crystalline cellulose (swelling binder), and L-HPC (first disintegrating agent) using a binding solution;

(2) performing granulation with addition of hydrophilic fumed silica (highly absorbent excipient) to the granulated product obtained in the step (1) (layering granulation step); and (3) performing granulation with addition of crospovidone (second disintegrating agent) to the granulated product obtained in the step (2) (layering granulation step).

Drying Method

Fluidized bed dryer (MDG-80: Fuji Paudal Co., Ltd.) 60° C., 45 minutes

TABLE 3

| Forming pressure (Kg/cm$^2$) | Placebo | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 135.1 | 23 | 101.8 | 68 | 70.1 | 17 |
| 250 | 111.7 | 17 | 89.2 | 65 | 59.7 | 15 |
| 200 | 87.7 | 14 | 77.1 | 35 | 50.2 | 11 |
| 150 | 64.5 | 11 | 56.6 | 20 | 39.1 | 8 |
| 100 | 47.5 | 12 | 35.8 | 13 | 23.9 | 7 |

Powder Characteristics of Obtained Dry Granulated Product

Average particle diameter: 83.1 μm
Compressibility: 29.1%
Tapped specific volume: 1.89 mL/g
Hydraulic Press Granules loaded into a die (11.3φ) were formed with S-04-127 manufactured by Riken Kiki Co., Ltd. (pressure receiving area: 6.42 cm$^2$). For example, a pressure of 300 kg/cm$^2$ corresponds to 18.87 kN on the basis of 300×9.8× 6.42.

This corresponds to about 11.8 kN in the case of an tablet, which serves as a standard in a formability evaluation method.

The resultant formed plate was evaluated for its hardness (hardness meter manufactured by Okada Seiko Co., Ltd.) and disintegration time (the Japanese Pharmacopoeia) with a disintegration tester manufactured by Toyama Sangyo Co., Ltd. and purified water at 37° C.

30% each of a placebo (containing no model particles), vitamin C-granulated product (VC 97: BASF), and EUDRAGIT-coated bitterness-masking model particles (functional particles, RSPO-FC: manufactured by Pharma Polytech Inc.) were mixed, and an 11 φ and 300 mg flat tablet was prepared with a hydraulic press (manufactured by Rigaku) and was evaluated.

Evaluation Results of Formability and Disintegrability of Example 4 (Aero/XL-10) (Table 4)

TABLE 4

| Forming pressure (Kg/cm$^2$) | Placebo | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 110.7 | 12 | 82.7 | 21 | 54.9 | 12 |
| 250 | 91.4 | 10 | 74.9 | 17 | 51.9 | 12 |
| 200 | 71.5 | 10 | 58.1 | 13 | 43.1 | 10 |
| 150 | 57.8 | 8 | 36.7 | 10 | 35.3 | 8 |
| 100 | 46.1 | 7 | 25.1 | 10 | 22.5 | 8 |

(5) Results of Continuous Tableting of Example 4 (Aero/XL-10) with Rotary Tableting Machine Including continuous tableting results of Example 4 and Comparative Example 1

Continuous Tableting

Continuous tableting sample: 1) Aero/XL-10 layering granulation product, high-speed agitation granulation product (VG) Placebo, Continuous tableting sample: 2) mixture for tableting obtained by mixing Example 4 with 30 parts by weight of bitterness-masking model particles (RSPO-FC functional particles: manufactured by Pharma Polytech Inc.), the functional particles containing carbazochrome sodium sulfonate as a model drug Purpose of Test Confirmation of Continuous Tabletability 0.4% of a lubricant magnesium stearate (St-Mg: manufactured by Taihei Chemical Industrial Co., Ltd.) was mixed, and continuous tableting was performed using a rotary tableting machine (VELS: Kikusui Seisakusho Ltd.). 8 φ12R Tableting results: no problem with tabletability (Table 5)

TABLE 5

| | Sample 1 (Example 4 Placebo) | | | Sample 2 (Example 4 + FC 30%) |
|---|---|---|---|---|
| Tableting pressure (kN) | 8.4 | 9.9 | 10.7 | 8 |
| Average weight (mg) | 205.9 | 200.9 | 201.1 | 199.6 |
| Weight variation CV (%) | 0.55 | 0.48 | 0.58 | 0.79 |
| Average tablet hardness (N) | 53.0 | 69.4 | 76.7 | 52.3 |
| Average disintegration time (sec) | 14.2 | 16.4 | 15.8 | 12.7 |
| Friability (%) | 0.4 | 0.3 | 0.25 | 0.29 |

Tableting results: Punch sticking or the like was not found in each case.

Continuous Tableting Results of Comparative Example 1 (Table 6)

TABLE 6

Powder characteristics (M/MP1):
D$_{50}$: 106.8 μm,
Compressibility (%): 28.8,
Tapped specific volume (mL/g): 1.85

| | S-1 | S-2 | S-3 |
|---|---|---|---|
| Tableting pressure (kN) | 3.8 | 7.0 | 9.7 |
| Average weight (M) | 206.4 | 203.0 | 204.6 |
| M-CV (%) | 0.60 | 0.74 | 0.65 |
| Average TH (N) | 45.1 | 61.9 | 81.3 |
| TH-CV (%) | 9.6 | 11.7 | 9.5 |
| Average DT (sec) | 19.0 | 22.8 | 31.2 |
| DT-CV (%) | 6.1 | 12.1 | 5.7 |
| Friability (%) | 0.26 | 0.29 | 0.11 |

The results are shown in FIG. 1.

(6) Comprehensive Evaluation based on Example 4 (Aero/XL-10)

A comprehensive comparison with Comparative Example 1 (no layering granulation), Comparative Example 2 (commercially available product A), and Comparative Example 3 (commercially available product B) was performed.

Contained model drugs (30 wt % in all cases) are as follows:
1. Placebo (no contained model drug),
2. Ethenzamide (ETZ-KS, ISP),
3. VC97 (BASF), 4. Acetaminophen (APAP: Hachidai Pharmaceutical Co., Ltd., average particle diameter $D_{50}$: 90 μm), 5. Bitterness-masking model particles (RSPO-FC: manufactured by Pharma Polytech Inc.).

Example 4 (Layering Granulation Aero/XL-10)
(Tables 7 and 8)

TABLE 7

| Forming pressure ($Kg/cm^2$) | Placebo | | ETZ-KS 30% | | VC97 30% | |
| --- | --- | --- | --- | --- | --- | --- |
| | Hardness (N) | Disintegration (sec) | Hardness (N) | Disintegration (sec) | Hardness (N) | Disintegration (sec) |
| 300 | 110.7 | 12 | 104.6 | 6 | 82.7 | 21 |
| 250 | 91.4 | 10 | 76.1 | 6 | 74.9 | 17 |
| 200 | 71.5 | 10 | 59.6 | 5 | 58.1 | 13 |
| 150 | 57.8 | 8 | 43.5 | 5 | 36.7 | 10 |
| 100 | 46.1 | 7 | 28.0 | 5 | 25.1 | 10 |

TABLE 8

| Forming pressure ($Kg/cm^2$) | APAP 30% | | RSPO-FC 30% | |
| --- | --- | --- | --- | --- |
| | Hardness (N) | Disintegration (sec) | Hardness (N) | Disintegration (sec) |
| 300 | 68.6 | 7 | 54.9 | 12 |
| 250 | 52.2 | 6 | 51.9 | 12 |
| 200 | 47.1 | 6 | 43.1 | 10 |
| 150 | 34.7 | 6 | 35.3 | 8 |
| 100 | 22.5 | 6 | 22.5 | 8 |

Comparative Example 1 (No Layering Granulation)
(Tables 9 and 10)

TABLE 9

| Forming pressure ($Kg/cm^2$) | Placebo | | ETZ-KS 30% | | VC97 30% | |
| --- | --- | --- | --- | --- | --- | --- |
| | Hardness (N) | Disintegration (sec) | Hardness (N) | Disintegration (sec) | Hardness (N) | Disintegration (sec) |
| 300 | 117.6 | 30 | 85.5 | 21 | 90.6 | 68 |
| 250 | 109.0 | 23 | 81.9 | 16 | 92.0 | 59 |
| 200 | 86.8 | 19 | 71.2 | 13 | 74.1 | 34 |
| 150 | 66.6 | 17 | 48.3 | 11 | 56.5 | 20 |
| 100 | 56.8 | 15 | 31.4 | 9 | 32.3 | 17 |

TABLE 10

| Forming pressure ($Kg/cm^2$) | APAP 30% | | RSPO-FC 30% | |
| --- | --- | --- | --- | --- |
| | Hardness (N) | Disintegration (sec) | Hardness (N) | Disintegration (sec) |
| 300 | 65.4 | 12 | 69.4 | 21 |
| 250 | 69.4 | 13 | 57.2 | 18 |
| 200 | 53.2 | 14 | 44.3 | 12 |
| 150 | 43.9 | 12 | 40.4 | 9 |
| 100 | 31.8 | 10 | 29.0 | 10 |

Comparative Example 2 (Commercially Available Product A) (Tables 11 and 12)

TABLE 11

| Forming pressure (Kg/cm$^2$) | Placebo | | ETZ-KS 30% | | VC97 30% | |
|---|---|---|---|---|---|---|
| | Hardness (N) | Disintegration (sec) | Hardness (N) | Disintegration (sec) | Hardness (N) | Disintegration (sec) |
| 300 | 135.2 | 34 | 107.8 | 200 | 111.4 | 224 |
| 250 | 105.8 | 22 | 101.9 | 157 | 97.6 | 124 |
| 200 | 84.3 | 17 | 84.3 | 38 | 85.5 | 65 |
| 150 | 73.5 | 10 | 68.6 | 19 | 69.0 | 29 |
| 100 | 56.8 | 10 | 48 | 10 | 46.9 | 18 |

TABLE 12

| Forming pressure (Kg/cm$^2$) | APAP 30% | | RSPO-FC 30% | |
|---|---|---|---|---|
| | Hardness (N) | Disintegration (sec) | Hardness (N) | Disintegration (sec) |
| 300 | 71.4 | 17 | 82.3 | 100 |
| 250 | 63.7 | 12 | 77.2 | 69 |
| 200 | 51.6 | 10 | 66.1 | 49 |
| 150 | 42.3 | 7 | 44.8 | 31 |
| 100 | 31.3 | 7 | 33.2 | 10 |

Comparative Example 3 (Commercially Available Product B) (Tables 13 and 14)

TABLE 13

| Forming pressure (Kg/cm$^2$) | Placebo | | ETZ-KS 30% | | VC97 30% | |
|---|---|---|---|---|---|---|
| | Hardness (N) | Disintegration (sec) | Hardness (N) | Disintegration (sec) | Hardness (N) | Disintegration (sec) |
| 300 | 80.4 | 246 | 77.4 | 275 | 95.7 | 269 |
| 250 | 112.7 | 193 | 61.7 | 230 | 93.1 | 258 |
| 200 | 92.1 | 108 | 53.9 | 207 | 81.4 | 209 |
| 150 | 68.6 | 98 | 41.2 | 130 | 67.0 | 169 |
| 100 | 58.8 | 90 | 31.4 | 72 | 42.7 | 111 |

TABLE 14

| Forming pressure (Kg/cm$^2$) | APAP 30% | | RSPO-FC 30% | |
|---|---|---|---|---|
| | Hardness (N) | Disintegration (sec) | Hardness (N) | Disintegration (sec) |
| 300 | 81.9 | 45 | 78.7 | 171 |
| 250 | 63.6 | 36 | 73.0 | 132 |
| 200 | 61.7 | 37 | 56.4 | 133 |
| 150 | 45.4 | 25 | 41.7 | 60 |
| 100 | 34.4 | 22 | 34.8 | 72 |

(7) Preparation Method for Comparative Example 1 (M/MP1) and Evaluation thereof

A preparation method was performed in accordance with the following reference: Shunji Uramatsu et al., Application of polyvinyl alcohol/acrylic acid/methyl methacrylate copolymer (POVACOAT) to orally rapidly disintegrating tablet, PHARM TECH JAPAN, 31(4), 52-57, (2015).

Raw Material

HMM: mannitol obtained by pulverizing D-mannitol (MM, Marine Crystal: Mitsubishi Shoji Foodtech Co., Ltd.) (speed mill: Fuji Paudal Co., Ltd., 1 mm herringbone)

Pea-25: PEARLITOL 25C (D-mannitol: Rocket)

Crystalline cellulose (CEOLUS PH101: Asahi Kasei Corporation)

Low-substituted hydroxypropyl cellulose (L-HPC, LH-21: Shin-Etsu Chemical Co., Ltd.)

PVA-based polymer: POVACOAT Type MP (Daido Chemical Industry Co., Ltd.)

Formulation and Loading Amount

| HMM/Pea-25 = 1/1 | 85% | 255 g |
|---|---|---|
| CEOLUS PH101 | 3.5% | 10.5 g |
| L-HPC LH21 | 10.5% | 31.5 g |
| POVACOAT Type MP | 1% | 3 g |

Granulation Method

High-speed agitation granulator (Vertical Granulator, VG FM-VG-01, Powrex)

Blade rotation speed: 250 rpm, chopper rotation speed: 1,500 rpm

Granulation time: 3 minutes

Amount of granulation liquid: 83.5 g of purified water

Drying Method

Fluidized bed dryer MDG-80 (Fuji Paudal Co., Ltd.)

Drying air temperature: 60° C., drying for 45 minutes

Powder Characteristics of Obtained Dry Granulated Product

Average particle diameter: 106.8 μm

Compressibility: 28.8%

Tapped specific volume: 1.85 mL/g

Hydraulic Press

Granules loaded into a die (11.3φ) were formed with S-04-127 manufactured by Riken Kiki Co., Ltd. (pressure receiving area: 6.42 cm$^2$). For example, a pressure of 300 kg/cm$^2$ corresponds to 18.87 kN on the basis of 300×9.8×6.42.

This corresponds to about 11.8 kN in the case of an tablet, which serves as a standard in a formability evaluation method.

The resultant formed plate was evaluated for its hardness (hardness meter manufactured by Okada Seiko Co., Ltd.) and disintegration time (the Japanese Pharmacopoeia) with a disintegration tester manufactured by Toyama Sangyo Co., Ltd. and purified water at 37° C.

30% each of a placebo (containing no model particles), vitamin C-granulated product (VC 97: BASF), and EUDRAGIT-coated bitterness-masking model particles (RSPO-FC: manufactured by Pharma Polytech Inc.) were mixed, and an 11 φ and 300 mg flat tablet was prepared with a hydraulic press (manufactured by Rigaku) and was evaluated.

Evaluation Results of Formability and Disintegrability of Comparative Example 1 (No Layering Granulation) (Table 15)

TABLE 15

| Forming pressure (Kg/cm²) | Placebo | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 117.6 | 30 | 90.6 | 68 | 69.4 | 21 |
| 250 | 109.0 | 23 | 92.0 | 59 | 57.2 | 18 |
| 200 | 86.8 | 19 | 74.1 | 34 | 44.3 | 12 |
| 150 | 66.6 | 17 | 56.5 | 20 | 40.4 | 9 |
| 100 | 56.8 | 15 | 32.3 | 17 | 29.0 | 10 |

(8) Addition Effect of Hardness-Modifying Additive in Functional Particle-Containing Tableting Test sample Example 4 (Aero/XL-10 layering granulation product: high-speed agitation granulation product (VG)) was mixed with 15% of microcrystalline cellulose (CEOLUS PH101: Asahi Kasei Corporation), and the resultant was mixed with 30 wt % each of a vitamin C-granulated product (VC 97: BASF) and EUDRAGIT-coated bitterness-masking model particles (RSPO-FC: manufactured by Pharma Polytech Inc.) to produce a granule for tableting.

The compositing of a composite granulated product (Example 4) was treatment involving the following steps:

(1) performing wet granulation by mixing D-mannitol (sugar or sugar alcohol), a PVA-based polymer (swelling binder), crystalline cellulose (swelling binder), and L-HPC (first disintegrating agent) using a binding solution;

(2) performing granulation with addition of hydrophilic fumed silica (highly absorbent excipient) to the granulated product obtained in the step (1) (layering granulation step); and (3) performing granulation with addition of crospovidone (second disintegrating agent) to the granulated product obtained in the step (2) (layering granulation step).

A granule for tableting was prepared through (4) a step of adding and mixing microcrystalline cellulose (hardness modifier) into the composite granulated product.

Each product was mixed with 30% of bitterness-masking model particles (RSPO-FC: manufactured by Pharma Polytech Inc.), and an 11 φ and 300 mg flat tablet was prepared with a hydraulic press (manufactured by Rigaku) and evaluated for its effectiveness.

Comparative Example 1 M/MP1 Premix VG Product

Results obtained using Example 4 (Tables 16 and 17)

TABLE 16

| Forming pressure (Kg/cm²) | Placebo PH101 15% | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 118.3 | 10 | 98.7 | 23 | 66.0 | 5 |
| 250 | 104.6 | 8 | 77.2 | 12 | 57.4 | 5 |
| 200 | 91.9 | 5 | 67.7 | 9 | 51.4 | 3 |
| 150 | 66.6 | 5 | 45.0 | 6 | 36.7 | 3 |
| 100 | 41.3 | 5 | 30.3 | 6 | 24.5 | 3 |

TABLE 17

| Forming pressure (Kg/cm²) | Placebo Without PH101 | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 110.7 | 12 | 82.7 | 21 | 54.9 | 12 |
| 250 | 91.4 | 10 | 74.9 | 17 | 51.9 | 12 |

TABLE 17-continued

| Forming pressure (Kg/cm²) | Placebo Without PH101 | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 200 | 71.5 | 10 | 58.1 | 13 | 43.1 | 10 |
| 150 | 57.8 | 8 | 36.7 | 10 | 35.3 | 8 |
| 100 | 46.1 | 7 | 25.1 | 10 | 22.5 | 8 |

Results obtained using Comparative Example 1 (Tables 18 and 19)

TABLE 18

| Forming pressure (Kg/cm²) | Placebo PH101 15% | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 130.1 | 15 | 113.9 | 64 | 79.6 | 19 |
| 250 | 115.1 | 16 | 84.6 | 60 | 65.1 | 18 |
| 200 | 90.6 | 12 | 79.7 | 33 | 52.6 | 11 |
| 150 | 74.4 | 12 | 56.2 | 17 | 43.0 | 8 |
| 100 | 48.8 | 9 | 35.0 | 13 | 31.6 | 7 |

TABLE 19

| Forming pressure (Kg/cm²) | Placebo Without PH101 | | VC97 30% | | RSPO-FC 30% | |
|---|---|---|---|---|---|---|
| | Hardness (N) | Disintegration (sec) | Hardness (N) | Disintegration (sec) | Hardness (N) | Disintegration (sec) |
| 300 | 117.6 | 30 | 90.6 | 68 | 69.4 | 21 |
| 250 | 109.0 | 23 | 92.0 | 59 | 57.2 | 18 |
| 200 | 86.8 | 19 | 74.1 | 34 | 44.3 | 12 |
| 150 | 66.6 | 17 | 56.5 | 20 | 40.4 | 9 |
| 100 | 56.8 | 15 | 32.3 | 17 | 29.0 | 10 |

(9) Dissolution Test Results

In order to confirm whether there was no adverse influence on the rupture of a film of the functional particles, the following test was performed using the Example 4 (Aero/XL-10) layering granulation particles.

Test Sample

Example 4 (Aero/XL-10) layering granulation product (high-speed agitation granulation product)

Bitterness-masking model particles (RSPO-FC: manufactured by Pharma Polytech Inc.), the bitterness-masking model particles (functional particles) containing carbazochrome sodium sulfonate as a model drug Tableting Conditions The premix particles (Example 4 (Aero/XL-10) layering granulation product) and 30% of RSPO-FC were mixed, and 0.4% of a lubricant: magnesium stearate (St-Mg: manufactured by Taihei Chemical Industrial Co., Ltd.) was mixed.

Tableting was performed with a rotary tableting machine (VELS: Kikusui Seisakusho Ltd.), 412R (target weight; 200 mg) at a tableting pressure of 8 kN.

Dissolution Test Conditions

Dissolution test of the Japanese Pharmacopoeia (method II, paddle: 100 rpm, 900 mL, 37° C., purified water)

A drug concentration was measured with a spectrophotometer (363 nm).

Tableting Results (Table 20)

There is no problem with tabletability.

TABLE 20

| | |
|---|---|
| Tableting pressure (kN) | 8 |
| Average weight (mg) | 199.6 |
| Weight variation CV (%) | 0.79 |
| Average tablet hardness (N) | 52.3 |
| Average disintegration time (sec) | 12.7 |
| Friability (%) | 0.29 |
| | (No cracking or chipping of tablet) |

Dissolution Test Results

The dissolution rate was not changed by tableting, and hence it was confirmed that there was no rupture of the film of the functional drug particles.

Figure 2:
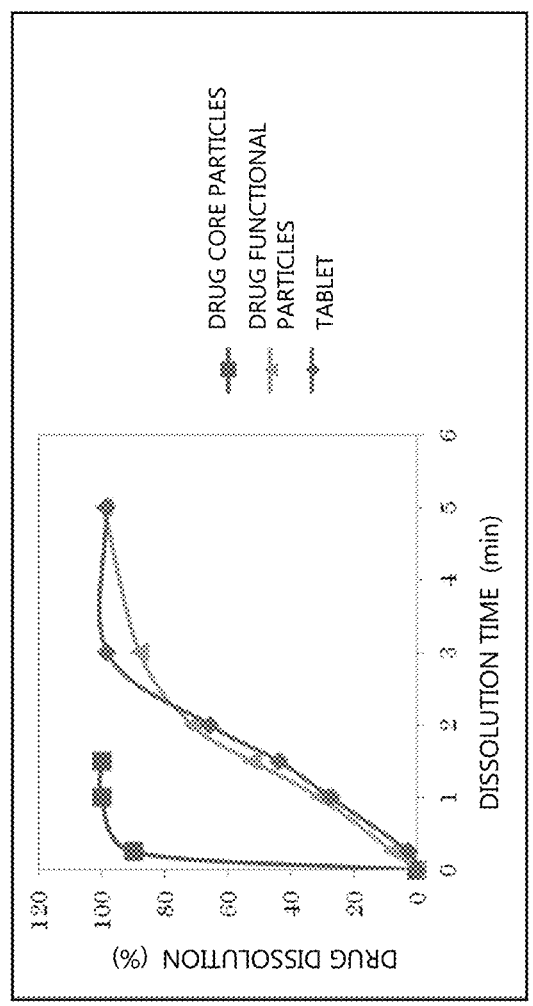
FIG. 2 is a graph for showing dissolution test results of Example 4 (Aero/XL-10).

The results are shown in FIG. 2.

(10) Results of Stability Test (40° C., 1 M)

Test Sample

Example 1: Aero/cons layering granulation product, high-speed agitation granulation product Example 4: Aero/XL-10 layering granulation product, high-speed agitation granulation product Comparative Example 1: M/MP1 high-speed agitation granulation product Comparative Example 2: commercially available product A Comparative Example 3: commercially available product C Into each sample, 30 wt % of spherical microcrystalline cellulose (CELPHERE CP102, Asahi Kasei Corporation) was incorporated as OD tablet functional model particles and 0.4% of St-Mg was incorporated as a lubricant, and an 412R and 200 mg tablet was prepared with a rotary tableting machine (VELS: Kikusui Seisakusho Ltd.).

The tableting pressure was adjusted so that the tablet hardness of each tablet was around 50 N.

Those test tablets were subjected to one-month evaluation at 40° C./75% RH (Tables 21 and 22).

TABLE 21

|  | Example 1 | | Example 4 | |
| --- | --- | --- | --- | --- |
|  | Hardness (N) | Disintegration (sec) | Hardness (N) | Disintegration (sec) |
| Initial value | 50.0 | 16 | 51.9 | 16 |
| After 1 month | 45.1 | 15 | 51.0 | 14 |
| Hardness retention rate (%) | 90.2 | | 98.3 | |

TABLE 22

|  | Comparative Example 1 | | Comparative Example 2 | | Comparative Example 3 | |
| --- | --- | --- | --- | --- | --- | --- |
|  | Hardness (N) | Disintegration (sec) | Hardness (N) | Disintegration (sec) | Hardness (N) | Disintegration (sec) |
| Initial value | 49.0 | 18 | 56.8 | 15 | 62.7 | 10 |
| After 1 month | 42.1 | 17 | 44.1 | 21 | 36.3 | 11 |
| Hardness Retention rate (%) | 85.9 | | 77.6 | | 57.9 | |

Hardness measurement: hardness meter manufactured by Okada Seiko Co., Ltd.

Disintegration time: measured in accordance with the Japanese Pharmacopoeia (purified water, 37° C.), Toyama Sangyo Co., Ltd.

The invention claimed is:

1. A manufacturing method for a composite granulated product including a sugar or a sugar alcohol, a swelling binder, a disintegrating agent, and a highly absorbent excipient, the manufacturing method comprising the steps of:
(1) performing wet granulation by mixing a sugar or a sugar alcohol, a swelling binder, and a first disintegrating agent using a binding solution to obtain a first wet granulated product;
(2) performing granulation with addition of a highly absorbent excipient to the first wet granulated product obtained in the step (1) to obtain a second wet granulated product; and
(3) performing granulation with addition of a second disintegrating agent to the second wet granulated product obtained in the step (2), the first disintegrating agent and the second disintegrating agent each being at least one kind of component selected from the group consisting of hydroxypropyl cellulose, crospovidone, starch, croscarmellose sodium, carmellose calcium, carmellose, partially pregelatinized starch, carboxymethyl starch sodium, and sodium starch glycolate.

2. The manufacturing method for a composite granulated product according to claim 1, wherein the sugar or the sugar alcohol is at least one kind of component selected from the group consisting of D-mannitol, trehalose, xylitol, erythritol, lactose, and sucrose.

3. The manufacturing method for a composite granulated product according to claim 1, wherein the swelling binder is at least one kind of component selected from the group consisting of a polyvinyl alcohol-based polymer, partially pregelatinized starch, hydroxypropyl cellulose, and crystalline cellulose.

4. The manufacturing method for a composite granulated product according to claim 1, wherein the swelling binder has an average particle diameter of from 10 μm to 200 μm.

5. The manufacturing method for a composite granulated product according to claim 1, wherein the highly absorbent excipient is at least one kind of component selected from the group consisting of light anhydrous silicic acid, hydrated silicon dioxide, calcium silicate, magnesium aluminometasilicate, starch, calcium carbonate, kaolin, silicic acid, potassium hydrogen phosphate, calcium hydrogen phosphate, sodium hydrogen phosphate, dipotassium phosphate, disodium phosphate, potassium dihydrogen phosphate, calcium dihydrogen phosphate, sodium dihydrogen phosphate, calcium lactate, magnesium aluminosilicate, calcium silicate, and magnesium silicate.

6. The manufacturing method for a composite granulated product according to claim 1, wherein the first disintegrating agent is hydroxypropyl cellulose, and the second disintegrating agent is at least one kind of component selected from the group consisting of starch, crospovidone, and croscarmellose sodium.

7. The manufacturing method for a composite granulated product according to claim 1, wherein the composite granulated product is a composite granulated product for an orally disintegrating tablet.

8. A manufacturing method for a granule for tableting, comprising
(4) a step of adding and mixing at least one kind of hardness modifier selected from the group consisting of crystalline cellulose, a D-mannitol granulated product, and isomalt into a composite granulated product obtained by the manufacturing method for a composite granulated product of claim 1.

9. The manufacturing method for a granule for tableting according to claim 8, wherein the granule for tableting is a granule for tableting for an orally disintegrating tablet.

10. A manufacturing method for a tablet, comprising mixing:
- a medicinal component and functional particles; and
- a composite granulated product obtained by the manufacturing method for a composite granulated product of claim 1, or
- a described granule for tableting obtained by the manufacturing method for a granule for tableting of claim 8.

11. The manufacturing method for a tablet according to claim 10, wherein the functional particles are at least one kind of component selected from the group consisting of bitterness-masking particles and sustained-release particles.

12. The manufacturing method for a tablet according to claim 10, further comprising adding and mixing a lubricant.

13. The manufacturing method for a tablet according to claim 10, wherein the tablet is an orally disintegrating tablet.

14. A composite granulated product, which is manufactured by the manufacturing method for a composite granulated product of claim 1.

15. A granule for tableting, which is manufactured by the manufacturing method for a granule for tableting of claim 8.

* * * * *